(12) United States Patent
Wallace et al.

(10) Patent No.: US 7,772,234 B2
(45) Date of Patent: Aug. 10, 2010

(54) BICYCLIC INHIBITORS OF MEK AND METHODS OF USE THEREOF

(75) Inventors: Eli Wallace, Lyons, CO (US); Hong Woon Yang, Superior, CO (US); James Blake, Longmont, CO (US)

(73) Assignee: Array Biopharma Inc., Boulder, CO (US)

( * ) Notice: Subject to any disclaimer, the term of this patent is extended or adjusted under 35 U.S.C. 154(b) by 1316 days.

(21) Appl. No.: 10/992,605

(22) Filed: Nov. 18, 2004

(65) Prior Publication Data

US 2005/0130976 A1 Jun. 16, 2005

Related U.S. Application Data

(60) Provisional application No. 60/523,270, filed on Nov. 19, 2003.

(51) Int. Cl.
| | |
|---|---|
| A01N 43/60 | (2006.01) |
| A61K 31/495 | (2006.01) |
| C07D 237/26 | (2006.01) |
| C07D 487/00 | (2006.01) |

(52) U.S. Cl. ..................... 514/248; 544/235
(58) Field of Classification Search ............ None
See application file for complete search history.

(56) References Cited

U.S. PATENT DOCUMENTS

| | | | |
|---|---|---|---|
| 5,231,094 A | 7/1993 | Bru-Magniez et al. | |
| 5,525,625 A | 6/1996 | Bridges et al. | |
| 6,310,060 B1 | 10/2001 | Barrett et al. | |
| 6,469,004 B1 | 10/2002 | Barrett et al. | |
| 6,506,798 B1 | 1/2003 | Barrett et al. | |
| 6,831,175 B2 * | 12/2004 | Li et al. | 546/187 |
| 2003/0004193 A1 | 1/2003 | Barrett et al. | |
| 2003/0045521 A1 | 3/2003 | Tecle | |
| 2003/0078428 A1 | 4/2003 | Barrett et al. | |
| 2003/0092748 A1 | 5/2003 | Barrett et al. | |
| 2003/0195183 A1 | 10/2003 | Zhilov | |
| 2003/0199511 A1 * | 10/2003 | Li et al. | 514/247 |
| 2003/0216460 A1 | 11/2003 | Wallace et al. | |
| 2003/0232869 A1 | 12/2003 | Wallace et al. | |
| 2004/0116710 A1 | 6/2004 | Wallace et al. | |

FOREIGN PATENT DOCUMENTS

| | | |
|---|---|---|
| WO | WO 95/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |
| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/44166 A1 | 6/2002 |
| WO | WO 03/051366 * | 6/2003 |
| WO | WO 03/077855 A2 | 9/2003 |
| WO | WO 03/077914 A1 | 9/2003 |

OTHER PUBLICATIONS

Vippagunta et al. Advanced Drug Delivery Reviews, 2001, 48, 3-26.*
M-C Viaud, et al. "Acylation of Oxazolo[4,5-b]Pyridin-2(3H)-Ones, 2-Phenyloxazolo[4,5-b]Pyridines and Pyrrolo[2,3-b]Pyridin-2(2H)-Ones"; Tetrahedron; 1997; pp. 5159-5168; vol. 53, No. 14; Elsevier Science Ltd.; Great Britain.
Moreau, et al. "Synthesis and Anticonvulsant Properties of Triazolo- and Imidazopyridazinyl Carboxamides and Carboxylic Acids" Bioorganic & Medicinal Chemistry; 1998; pp. 983-991; vol. 6; Elsevier Science Ltd.
Bachman, G. Bryant, et al., Further Studies of Aminobenzacridines, Journal of Organic Chemistry, vol. 13, 1948. pp. 89-96, pp. 93-96.

* cited by examiner

*Primary Examiner*—James O Wilson
*Assistant Examiner*—Noble Jarrell
(74) *Attorney, Agent, or Firm*—John R. Moore; Hogan & Hartson

(57) ABSTRACT

Disclosed are compounds of the Formula I

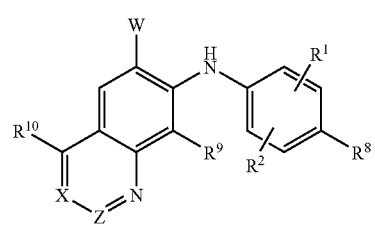

and pharmaceutically acceptable salts and prodrugs thereof, wherein $R^1$, $R^2$, $R^8$, $R^9$ and $R^{10}$, W, X, and Z are as defined in the specification. Such compounds are MEK inhibitors and useful in the treatment of hyperproliferative diseases, such as cancer and inflammation, in mammals, and inflammatory conditions. Also disclosed are methods of using such compounds in the treatment of hyperproliferative diseases in mammals and pharmaceutical compositions containing such compounds.

32 Claims, 9 Drawing Sheets

BICYCLIC INHIBITORS OF MEK AND METHODS OF USE THEREOF

CROSS-REFERENCE TO RELATED APPLICATIONS

This application claims the benefit of U.S. Provisional Application Ser. No. 60/523,270, filed Nov. 19, 2003, which is incorporated herein in its entirety by reference.

BACKGROUND OF THE INVENTION

1. Field of the Invention

This invention relates to a series of novel heterocyclic compounds that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

2. Description of the State of the Art

Cell signaling through growth factor receptors and protein kinases is an important regulator of cell growth, proliferation and differentiation. In normal cell growth, growth factors, through receptor activation (i.e., PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222and S226 for MEK2) (Ahn et al., *Methods in Enzymology*, 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology*, 2001, 332, 417-431). Phosphorylated ERK dimerizes and then translocates to the nucleus where it accumulates (Khokhlatchev et al., *Cell*, 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell*, 2000, 6, 1343-1354). Overall, treatment of cells with growth factors leads to the activation of ERK1 and 2 which results in proliferation and, in some cases, differentiation (Lewis et al., *Adv. Cancer Res.*, 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science*, 1993, 260, 1834-1837). Recently, bRaf mutations have been identified in more than 60% of malignant melanoma (Davies, H. et al., *Nature*, 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene*, 1999, 18, 813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature—Medicine*, 1999, 5 (7), 810-816; Trachet et al., AACR Apr. 6-10, 2002, Poster #5426; Tecle, H., IBC 2nd International Conference of Protein Kinases, Sep. 9-10, 2002), block static allodynia in animals (WO 01/05390 published Jan. 25, 2001) and inhibit growth of acute myeloid leukemia cells (Milella et al., *J. Clin. Invest.*, 2001, 108 (6), 851-859).

Small molecule inhibitors of MEK have been disclosed, including in U.S. Patent Publication Nos. 2003/0232869, 2004/0116710, and 2003/0216460, and U.S. patent application Ser. Nos. 10/654,580 and 10/929,295, each of which is hereby incorporated by reference. At least fifteen additional patent applications have appeared in the last several years. See, for example: U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

SUMMARY OF THE INVENTION

This invention provides for novel heterocyclic compounds and pharmaceutically acceptable salts and prodrugs thereof that are useful in the treatment of hyperproliferative diseases. Specifically, one embodiment of the present invention provides compounds of Formulas I-II that act as MEK inhibitors.

More specifically, the present invention provides compounds of the Formulas I-II:

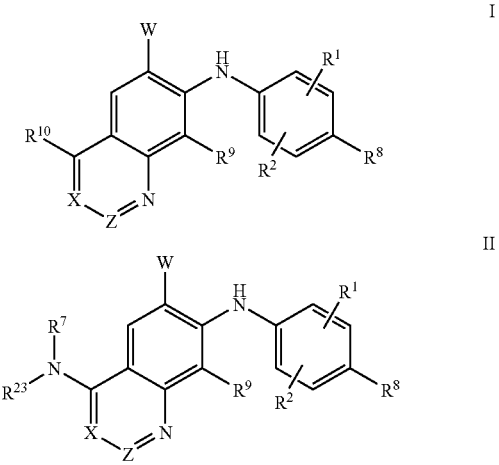

and pharmaceutically accepted salts, prodrugs and solvates thereof, wherein:

X and Z are independently $CR^3$ or N;

$R^1$, $R^2$, $R^8$, $R^9$ and $R^{10}$ are independently hydrogen, hydroxy, halogen, cyano, nitro, trifluoromethyl, difluoromethyl, fluoromethyl, trifluoromethoxy, difluoromethoxy, trifluoromethoxy, azido, $—SR^{11}$, $—OR^3$, $—C(O)R^3$, $—C(O)OR^3$, $—NR^4C(O)OR^6$, $—OC(O)R^3$, $—NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on a aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on a aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl, or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —$NR^{11}SO_2R^{14}$, —$SO_{12}NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on a aryl or heteroaryl), halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

$R^7$ and $R^{15}$ are hydroxy, halogen, trifluoromethyl, difluoromethyl, fluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, $OR^3$, $NR^3R^4$, aryl, arylalkyl, heteroaryl, heteroarylalkyl, heterocyclyl, or heterocyclylalkyl, wherein any of said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from oxo (with the proviso that it is not substituted on a aryl or heteroaryl), halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$N^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, cycloalkyl, cycloalkylalkyl, heterocyclyl, and heterocyclylalkyl, and wherein said aryl, heteroaryl, arylalkyl, heteroarylalkyl, cycloalkyl, cycloalkylalkyl, heterocyclyl or heterocyclylalkyl rings may be further substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

or $R^7$ and $R^{15}$ together with the atom to which they are attached form a 4 to 10 membered aryl, carbocyclic, heteroaryl or heterocyclic ring, wherein any of said aryl, carbocyclic, heteroaryl or heterocyclic rings are optionally substituted with one or more groups independently selected from halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, cycloalkyl, cycloalkylalkyl, heterocyclyl, and heterocyclylalkyl;

$R^{11}$, $R^{12}$ and $R^{13}$ independently are hydrogen, lower alkyl, lower alkenyl, aryl and arylalkyl, and $R^{14}$ is lower alkyl, lower alkenyl, aryl and arylalkyl;

or any two of $R^{11}$, $R^{12}$, $R^{13}$ or $R^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —C(O)OR³, —C(O)NR³R⁴, —C(O)NR⁴OR³, —C(O)NR⁴OR³, —C(O)R⁴OR³, —C(O)NR⁴SO₂R³, —C(O)(C₃-C₁₀ cycloalkyl), —C(O)(C₁-C₁₀ alkyl), —C(O)(aryl), —C(O)(heteroaryl), —C(O)(heterocyclyl) or CR³OR³ wherein any of said heteroaryl, heterocyclyl, —C(O)OR³, —C(O)NR³R⁴, —C(O)NR⁴OR³, —C(O)R⁴OR³, —C(O)NR⁴SO₂R³, —C(O)(C₃-C₁₀ cycloalkyl), —C(O)(C₁-C₁₀ alkyl), —C(O)(aryl), —C(O)(heteroaryl), —C(O)(heterocyclyl) and CR³OR³ are optionally substituted with one or more groups independently selected from halogen, cyano, nitro, azido, —NR³R⁴, —OR³, C₁-C₁₀ alkyl, C₂-C₁₀ alkenyl, C₂-C₁₀ alkynyl, cycloalkyl and heterocycloalkyl, wherein any of said C₁-C₁₀ alkyl, C₂-C₁₀ alkenyl, C₂-C₁₀ alkynyl, cycloalkyl and heterocycloalkyl are optionally substituted with 1 or more groups independently selected from —NR³R⁴ and —OR³;

m is 0, 1, 2, 3, 4 or 5; and j is 0, 1 or 2.

In another embodiment, the present invention provides compositions that inhibit MEK comprising compounds of Formulas I-II.

The invention is also directed to pharmaceutically acceptable prodrugs, pharmaceutically active metabolites, and pharmaceutically acceptable salts of compounds of Formula I-II. Methods of making the compounds of Formula I-II are also described.

In yet another embodiment, the present invention provides a method of using the compounds of this invention to treat diseases or medical conditions mediated by MEK, such as cancer. For example, this invention provides a method for treatment of a hyperproliferative disorder or an inflammatory condition in a mammal comprising administrating to said mammal one or more compounds of Formulas I-II or a pharmaceutically acceptable salt or prodrug thereof in an amount effective to treat said hyperproliferative disorder.

In a further aspect the present invention provides treating or preventing an MEK-mediated condition, comprising administering to a human or animal in need thereof a pharmaceutical composition comprising a compound of Formula I-II or a pharmaceutically-acceptable salt or in vivo cleavable prodrug thereof in an amount effective to treat or prevent said MEK-mediated condition.

The inventive compounds may further be used advantageously in combination with other known therapeutic agents.

The invention also relates to pharmaceutical compositions comprising an effective amount of an agent selected from compounds of Formulas I-II or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
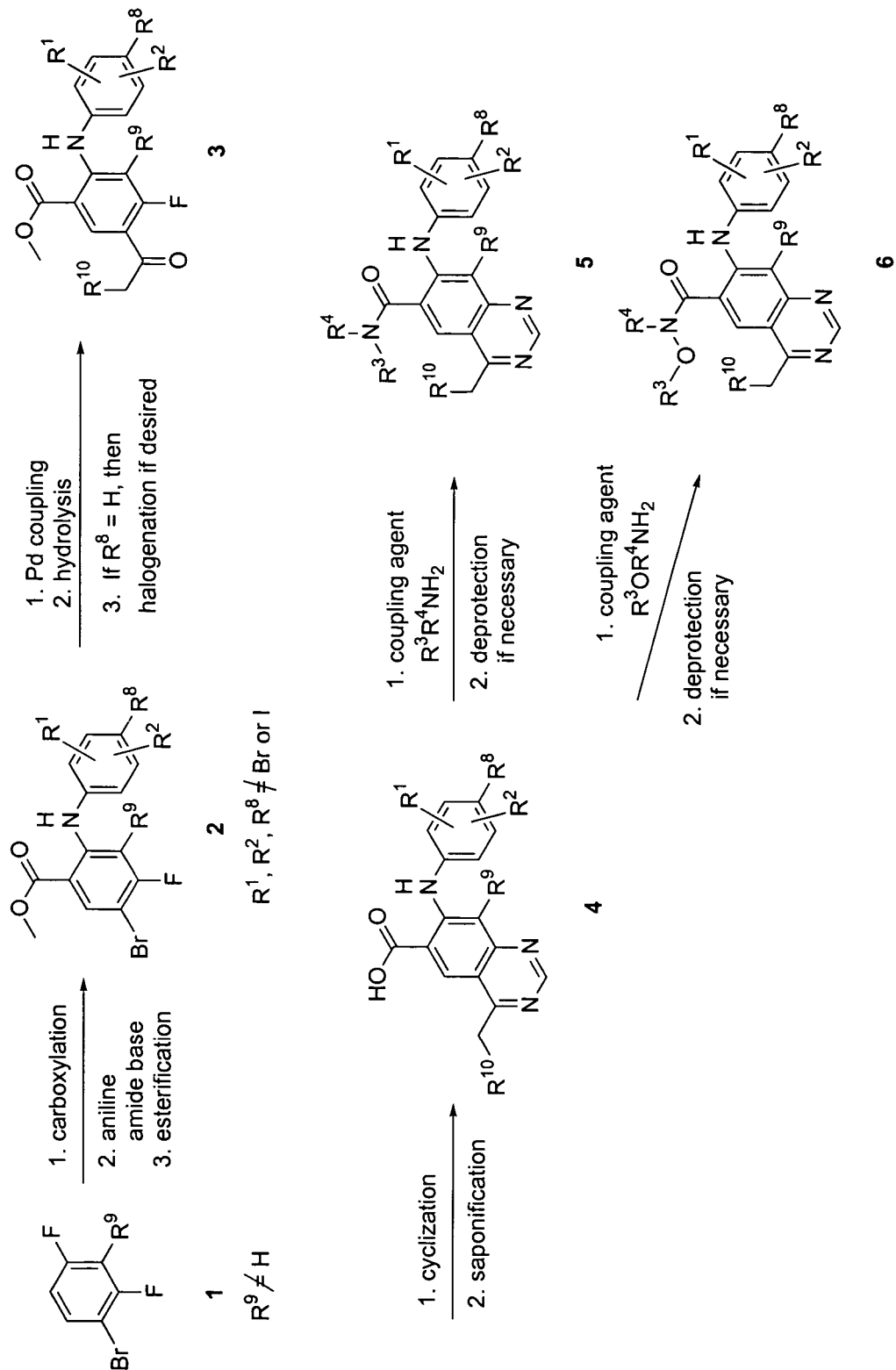
FIG. 1 shows a reaction scheme for the synthesis of compounds 4-6.

The inventive compounds of the Formulas I-II and the pharmaceutically acceptable salts and prodrugs thereof of this invention are useful in the treatment of hyperproliferative diseases. Specifically, one embodiment of the present invention relates to compounds of Formula I-II that act as MEK inhibitors. In general, one embodiment of the invention provides compounds having the general Formula I:

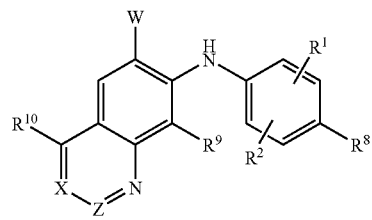

and pharmaceutically accepted salts, prodrugs and solvates thereof, wherein:

X and Z are independently CR³ or N;

R¹, R², R⁸, R⁹ and R¹⁰ are independently hydrogen, halogen, cyano, nitro, trifluoromethyl, difluoromethoxy, trifluoromethoxy, azido, —OR³, —C(O)R³, —C(O)OR³, NR⁴C(O)OR⁶, —OC(O)R³, —NR⁴SO₂R⁶, —SO₂NR³R⁴, —NR⁴C(O)R³, —C(O)NR³R⁴, —NR⁵C(O)NR³R⁴, —NR⁵C(NCN)NR³R⁴, —NR³R⁴, C₁-C₁₀ alkyl, C₂-C₁₀ alkenyl, C₂-C₁₀ alkynyl, C₃-C₁₀ cycloalkyl, C₃-C₁₀ cycloalkylalkyl, —S(O)ⱼ(C₁-C₆ alkyl), —S(O)ⱼ(CR⁴R⁵)ₘ-aryl, aryl, arylalkyl, heteroaryl, heteroarylalkyl, heterocyclyl, heterocyclylalkyl, —O(CR⁴R⁵)ₘ-aryl, —NR⁴(CR⁴R⁵)ₘ-aryl, —O(CR⁴R⁵)ₘ-heteroaryl, —NR⁴(CR⁴R⁵)ₘ-heteroaryl, —O(CR⁴R⁵)ₘ-heterocyclyl or —NR⁴(CR⁴R⁵)ₘ-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR⁴SO₂R⁶, —SO₂NR³R⁴, —C(O)R³, —C(O)OR³, —OC(O)R³, —NR⁴C(O)OR⁶, —NR⁴C(O)R³, —C(O)NR³R⁴, —NR³R⁴, —NR⁵C(O)NR³R⁴, —NR⁵C(NCN)

NR³R⁴, —OR³, aryl, heteroaryl, arylalkyl, heteroarylalkyl, heterocyclyl, and heterocyclylalkyl;

R³ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR¹⁵SO₂R¹⁸, —SO₂NR¹⁵R¹⁶, —C(O)R¹⁵, C(O)OR¹⁵, —OC(O)R¹⁵, —NR¹⁵C(O)OR¹⁸, —NR¹⁵C(O)R¹⁶, —C(O)NR¹⁵R¹⁶, —SR¹⁵, —S(O)R¹⁸, —SO₂R¹⁸, —NR¹⁵R¹⁶, —NR¹⁵C(O)NR¹⁶R¹⁷, —NR¹⁵C(NCN)NR¹⁶R¹⁷, —OR¹⁵, aryl, heteroaryl, arylalkyl, heteroarylalkyl, heterocyclyl, and heterocyclylalkyl, or R³ and R⁴ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR¹⁵SO₂R¹⁸, —SO₂NR¹⁵R¹⁶, —C(O)R¹⁵, —C(O)OR¹⁵, —OC(O)R¹⁵, —NR¹⁵C(O)OR¹⁸, —NR¹⁵C(O)R¹⁶, —C(O)NR¹⁵R¹⁶, —SO₂R¹⁸, —NR¹⁵R¹⁶, —NR¹⁵C(O)NR¹⁶R¹⁷, —NR¹⁵C(NCN)NR¹⁶R¹⁷, —OR¹⁵, aryl, heteroaryl, arylalkyl, heteroarylalkyl, heterocyclyl, and heterocyclylalkyl;

R¹⁵, R¹⁶ and R¹⁷ independently are hydrogen, lower alkyl, lower alkenyl, aryl and arylalkyl, and R¹⁸ is lower alkyl, lower alkenyl, aryl and arylalkyl, or any two of R⁵, R¹⁶, R¹⁷ or R¹⁸ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

R⁴ and R⁵ independently are hydrogen or $C_1$-$C_6$ alkyl, or

R⁴ and R⁵ together with the atom to which they are attached form a 4 to 10 membered carbocyclic, heteroaryl or heterocyclic ring, wherein any of said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR¹⁵O₂R¹⁸, —SO₂NR¹⁵R¹⁶, —C(O)R¹⁸, —C(O)OR¹⁵, —OC(O)R¹⁵, —NR¹⁵C(O)OR¹⁸, —NR¹⁵C(O)R¹⁶, —C(O)NR¹⁵R¹⁶, —SO₂R¹⁸, —NR¹⁵R¹⁶, —NR¹⁵C(O)NR¹⁶R¹⁷, —NR¹⁵C(NCN)NR¹⁶R¹⁷, —OR¹⁵, aryl, heteroaryl, arylalkyl, heteroarylalkyl, heterocyclyl, and heterocyclylalkyl;

R⁶ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR¹⁵SO₂R¹⁸, —SO₂NR¹⁵R¹⁶, —C(O)R¹⁵, —C(O)OR¹⁵, —OC(O)R¹⁵, —NR¹⁵C(O)OR¹⁸, —NR¹⁵C(O)R¹⁶, —C(O)NR¹⁵R¹⁶, —SO₂R¹⁸, —NR¹⁵R¹⁶, —NR¹⁵C(O)NR¹⁶R¹⁷, —NR¹⁵C(NCN)NR¹⁶R¹⁷, —OR¹⁵, aryl, heteroaryl, arylalkyl, heteroarylalkyl, heterocyclyl, and heterocyclylalkyl;

R¹¹, R¹² and R¹³ independently are hydrogen, lower alkyl, lower alkenyl, aryl and arylalkyl, and R¹⁴ is lower alkyl, lower alkenyl, aryl and arylalkyl, or any two of R¹¹, R¹², R¹³ or R¹⁴ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

m is 0, 1, 2, 3, 4 or 5;

n is 1 or 2; and j is 0, 1 or 2.

FIGS. 1, 3, 4, 6, 7 and 9 show non-limiting examples of the synthesis of compounds of this invention having the general Formula I.

In addition to compounds of the general Formula I, this invention further includes compounds of the general Formula II:

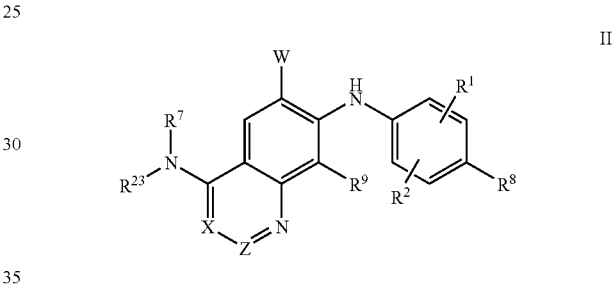

and pharmaceutically accepted salts, prodrugs and solvates thereof, where:

X and Z are independently CR³ or N;

R¹, R², R⁸, and R⁹ are independently hydrogen, halogen, cyano, nitro, trifluoromethyl, difluoromethoxy, trifluoromethoxy, azido, —OR³, —C(O)R³, —C(O)OR³, NR⁴C(O)OR⁶, —OC(O)R³, —NR⁴SO₂R⁶, —SO₂NR³R⁴, —NR⁴C(O)R³, —C(O)NR³R⁴, —NR⁵C(O)NR³R⁴, —NR⁵C(NCN)NR³R⁴, —NR³R⁴, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$(CR⁴R⁵)$_m$-aryl, aryl, arylalkyl, heteroaryl, heteroarylalkyl, heterocyclyl, heterocyclylalkyl, —O(CR⁴R⁵)$_m$-aryl, —NR⁴(CR⁴R⁵)$_m$-aryl, —O(CR⁴R⁵)$_m$-heteroaryl, —NR⁴(CR⁴R⁵)$_m$-heteroaryl, —O(CR⁴R⁵)$_m$-heterocyclyl or —NR⁴(CR⁴R⁵)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR⁴SO₂R⁶, —SO₂NR³R⁴, —C(O)R³, —C(O)OR³, —OC(O)R³, —NR⁴C(O)OR⁶, —NR⁴C(O)R³, —C(O)NR³R⁴, —NR³R⁴, —NR⁵C(O)NR³R⁴, —NR⁵C(NCN)NR³R⁴, —OR³, aryl, heteroaryl, arylalkyl, heteroarylalkyl, heterocyclyl, and heterocyclylalkyl;

R³ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, $-NR^{15}SO_2R^{18}$, $-SO_2NR^{15}R^{16}$, $-C(O)R^{15}$, $C(O)OR^{15}$, $-OC(O)R^{15}$, $-NR^{15}C(O)OR^{18}$, $-NR^{15}C(O)R^{16}$, $-C(O)NR^{15}R^{16}$, $-SR^{15}$, $-S(O)R^{18}$, $-SO_2R^{18}$, $-NR^{15}R^{16}$, $-NR^{15}C(O)NR^{16}R^{17}$, $-NR^{15}C(NCN)NR^{16}R^{17}$, $-OR^{15}$, aryl, heteroaryl, arylalkyl, heteroarylalkyl, heterocyclyl, and heterocyclylalkyl, or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, $-NR^{15}SO_2R^{18}$, $-SO_2NR^{15}R^{16}$, $-C(O)R^{15}$, $-C(O)OR^{15}$, $-OC(O)R^{15}$, $-NR^{15}C(O)OR^{18}$, $-NR^{15}C(O)R^{16}$, $-C(O)NR^{15}R^{16}$, $-SO_2R^{18}$, $-NR^{15}R^{16}$, $-NR^{15}C(O)NR^{16}R^{17}$, $-NR^{15}C(NCN)NR^{16}R^{17}$, $-OR^{15}$, aryl, heteroaryl, arylalkyl, heteroarylalkyl, heterocyclyl, and heterocyclylalkyl;

$R^{15}$, $R^{16}$ and $R^{17}$ independently are hydrogen, lower alkyl, lower alkenyl, aryl and arylalkyl, and $R^{18}$ is lower alkyl, lower alkenyl, aryl and arylalkyl, or any two of $R^{15}$, $R^{16}$, $R^{17}$ or $R^{18}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic, heteroaryl or heterocyclic ring, wherein any of said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, $-NR^{15}O_2R^{18}$, $-SO_2NR^{15}R^{16}$, $-C(O)R^{18}$, $-C(O)OR^{15}$, $-OC(O)R^{15}$, $-NR^{15}C(O)OR^{18}$, $-NR^{15}C(O)R^{16}$, $-C(O)NR^{15}R^{16}$, $-SO_2R^{18}$, $-NR^{15}R^{16}$, $-NR^{15}C(O)NR^{16}R^{17}$, $-NR^{15}C(NCN)NR^{16}R^{17}$, $-OR^{15}$, aryl, heteroaryl, arylalkyl, heteroarylalkyl, heterocyclyl, and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, $-NR^{15}SO_2R^{18}$, $-SO_2NR^{15}R^{16}$, $-C(O)R^{15}$, $-C(O)OR^{15}$, $-OC(O)R^{15}$, $-NR^{15}C(O)OR^{18}$, $-NR^{15}C(O)R^{16}$, $-C(O)NR^{15}R^{16}$, $-SO_2R^{18}$, $-NR^{15}R^{16}$, $-NR^{15}C(O)NR^{16}R^{17}$, $-NR^{15}C(NCN)NR^{16}R^{17}$, $-OR^{15}$, aryl, heteroaryl, arylalkyl, heteroarylalkyl, heterocyclyl, and heterocyclylalkyl;

$R^{11}$, $R^{12}$ and $R^{13}$ independently are hydrogen, lower alkyl, lower alkenyl, aryl and arylalkyl, and $R^{14}$ is lower alkyl, lower alkenyl, aryl and arylalkyl, or any two of $R^{11}$, $R^{12}$, $R^{13}$ or $R^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^7$ and $R^{15}$ are hydroxy, halogen, trifluoromethyl, difluoromethyl, fluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, $OR^3$, $NR^3R^4$, aryl, arylalkyl, heteroaryl, heteroarylalkyl, heterocyclyl, or heterocyclylalkyl, wherein any of said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, cycloalkyl, cycloalkylalkyl, heterocyclyl, and heterocyclylalkyl, and wherein any of said aryl, heteroaryl, arylalkyl, heteroarylalkyl, cycloalkyl, cycloalkylalkyl, heterocyclyl or heterocyclylalkyl rings may be further substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

or $R^7$ and $R^{15}$ together with the atom to which they are attached form a 4 to 10 membered aryl, carbocyclic, heteroaryl or heterocyclic ring, wherein any of said aryl, carbocyclic, heteroaryl or heterocyclic rings are optionally substituted with one or more groups independently selected from halogen, cyano, nitro, trifluoromethyl, difluoromethyl, fluoromethyl, fluoromethoxy, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, cycloalkyl, cycloalkylalkyl, heterocyclyl, and heterocyclylalkyl;

m is 0, 1, 2, 3, 4 or 5;

n is 1 or 2; and j is 0, 1 or 2.

Figure 2:
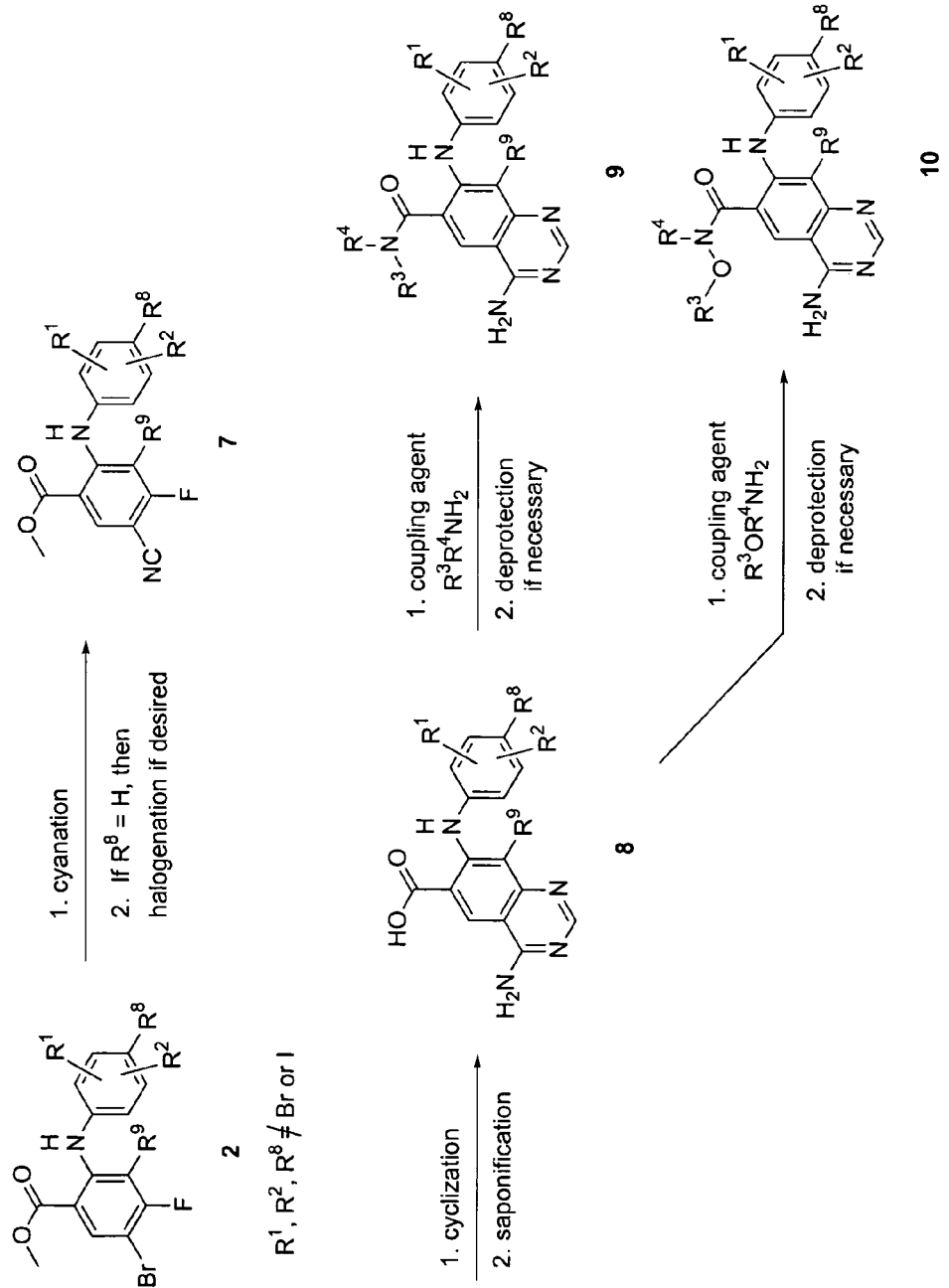
FIG. 2 shows a reaction scheme for the synthesis of compounds 8-10.
Figure 5:
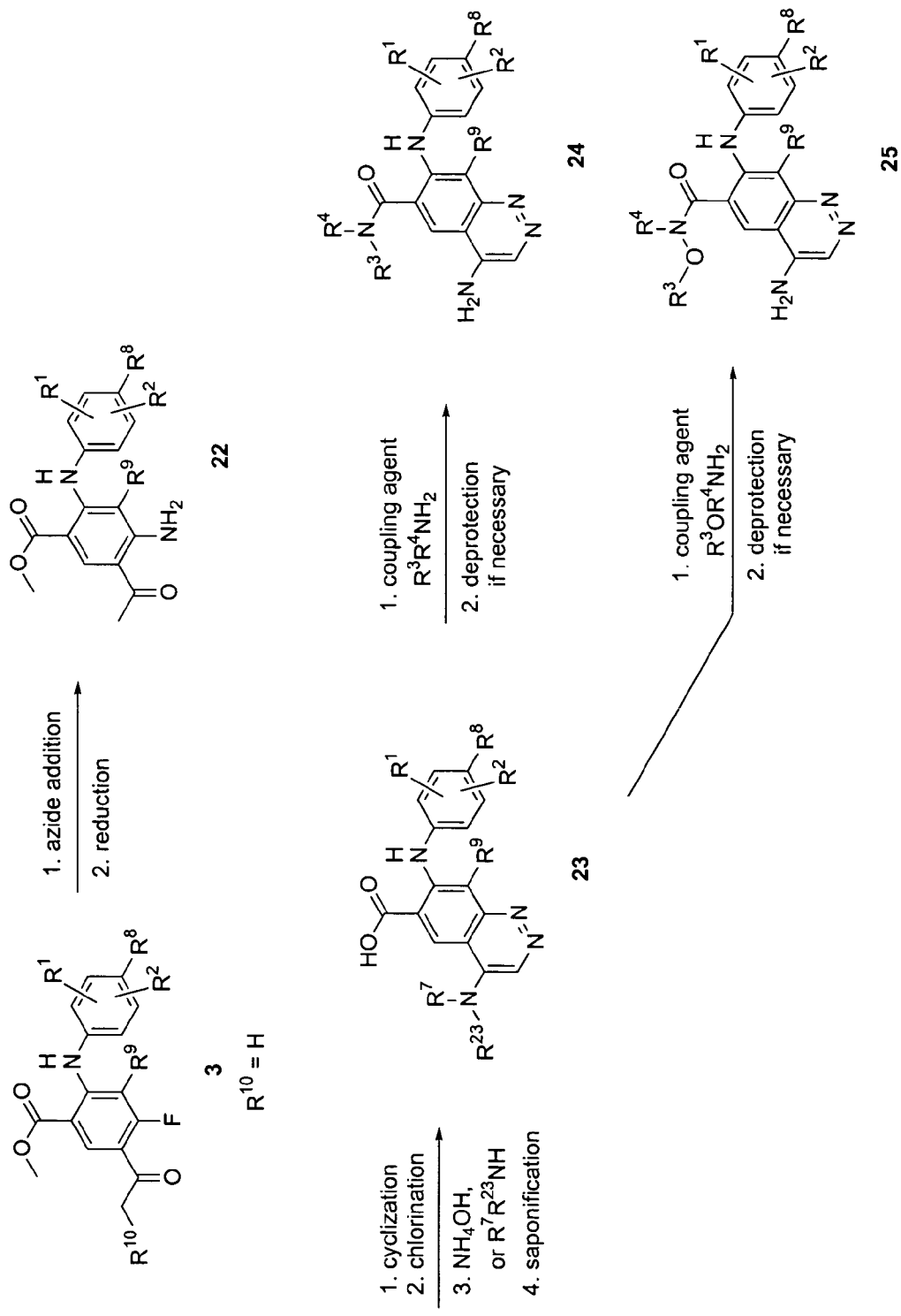
FIG. 5 shows a reaction scheme for the synthesis of compounds 23-25.
Figure 8:
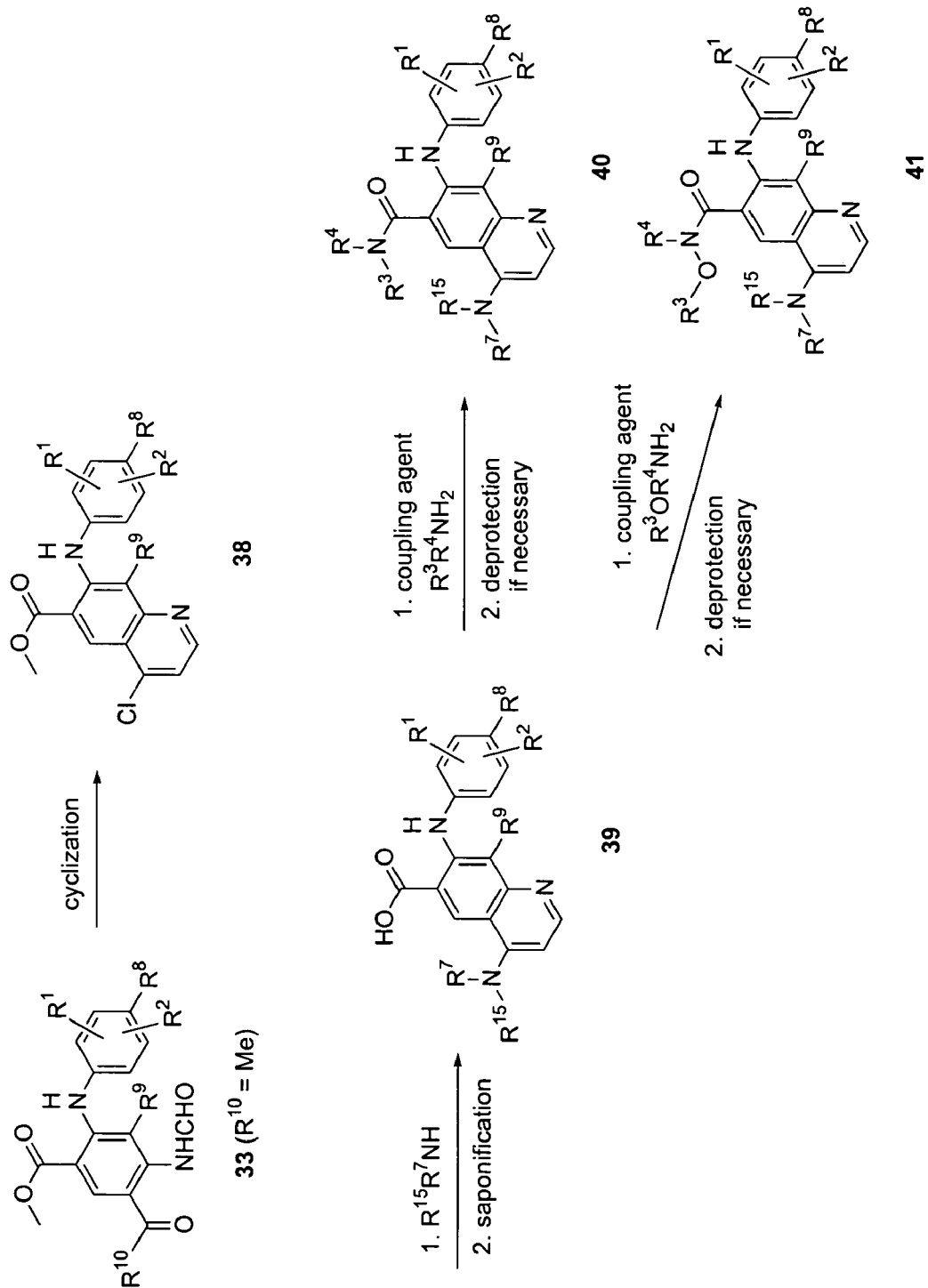
FIG. 8 shows a reaction scheme for the synthesis of compounds 39-41.

FIGS. 2, 5 and 8 show non-limiting examples of the synthesis of compounds of this invention having the general Formula II.

In one preferred embodiment, W is selected from

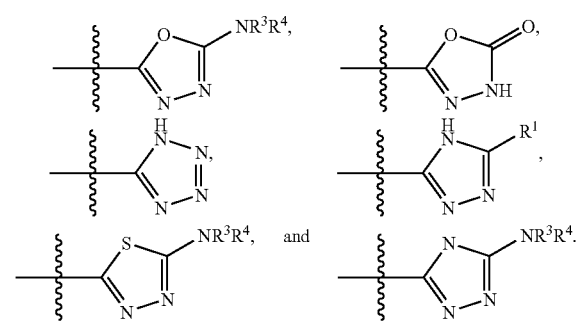

The terms "$C_1$-$C_{10}$ alkyl", "alkyl" and "lower alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "$C_2$-$C_{10}$ alkenyl", "lower alkenyl" and "alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "$C_2$-$C_{10}$ alkynyl", "lower alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "allyl" refers to a radical having the formula RC=CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The terms "carbocycle," "carbocyclyl," "cycloalkyl" or "$C_3$-$C_{10}$ cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "hetercyclyl" refer to a saturated or partially unsaturated carbocyclic radical of 3 to 10 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes bicyclic and tricyclic fused ring systems which include a heterocycle fused to an aromatic group. "Heterocycloalkyl" also includes radicals where heterocycle radicals are fused with one or more carbocyclic or heterocyclic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

The term "halogen" represents fluorine, bromine, chlorine, and iodine.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

The term "amino acid residue" includes, but is not limited to, the 20 naturally occurring amino acids commonly designated by three letter symbols, and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone.

In general, the various moieties or functional groups of the compounds of Formulas I-II may be optionally substituted by one or more substituents. Examples of substituents suitable for purposes of this invention include, but are not limited to, oxo, (with the proviso that the oxo substituent is not on an aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, where $R^3$, $R^4$, $R^5$ and $R^6$ are as defined herein.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the compounds of the present invention, where a term such as $(CR^4R^5)_m$ is used, $R^4$ and $R^5$ may vary with each iteration of m above 1. For instance, where m is 2, the term $(CR^4R^5)_m$ may equal —$CH_2CH_2$— or —$CH(CH_3)C(CH_2CH_3)(CH_2CH_2CH_3)$— or any number of similar moieties falling within the scope of the definitions of $R^4$ and $R^5$.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and pure enantiomers of the Formulas I-II. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

This invention also encompasses pharmaceutical compositions containing a compound of Formula I-II and methods of treating proliferative disorders, or abnormal cell growth, by administering compounds of the present invention. Compounds of the present invention having free amino, amido, hydroxy or carboxylic groups can be converted into pharmaceutically acceptable prodrugs.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of Formula I-II covalently joined to a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group to a phosphate ester, hemisuccinate, dimethylaminoacetate, or phosphoryloxymethyloxycarbonyl, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, -P(O)(O($C_1$-$C_6$)alkyl)$_2$ or glycosyl (the radical resulting from the removal of a hydroxyl group of the hemiacetal form of a carbohydrate).

Free amines can also be derivatized as amides, sulfonamides or phosphonamides. For example, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY wherein Y is H, ($C_1$-$C_6$)alkyl or benzyl, —C(OY$_0$)Y$_1$ wherein Y$_0$ is ($C_1$-$C_4$) alkyl and Y$_1$ is ($C_1$-$C_6$) alkyl, carboxy($C_1$-$C_6$)alkyl, amino($C_1$-$C_4$)alkyl or mono-N- or di-N,N-($C_1$-$C_6$)alkylaminoalkyl, —C($Y_2$)$Y_3$ wherein $Y_2$ is H or methyl and $Y_3$ is mono-N- or di-N,N-($C_1$-$C_6$)alkylamino, morpholino, piperidin-1-yl or pyrrolidin-1-yl.

All of these prodrug moieties may incorporate groups including but not limited to ether, amine and carboxylic acid functionalities.

In addition, the invention also includes solvates, pharmaceutically active metabolites, and pharmaceutically acceptable salts of compounds of Formulas I-II.

The term "solvate" refers to an aggregate of a molecule with one or more solvent molecules.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

A "pharmaceutically acceptable salt" as used herein, unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylaamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

The inventive compounds may be prepared using the reaction routes and synthesis schemes as described below, employing the techniques available in the art using starting materials that are readily available or can be synthesized using methods known in the art.

Illustrations of the preparation of compounds of the present invention are shown in FIGS. 1-9.

FIG. 1 illustrates the synthesis of compounds of Formula I of the present invention. 5-Bromobenzoic acid methyl ester 2 is prepared in a three-step procedure from the bromofluorobenzene 1. Carboxylation of the compound 1 is accomplished in a suitable organic solvent such as THF or $Et_2O$ using saturated solution of $CO_2$ in THF and an amide base such as LDA, LiHMDS, NaHMDS, or KHMDS at appropriate temperatures. Incorporation of the appropriate aniline moiety to give carboxylic acid intermediate can be achieved by $S_NAr$ reaction. This is done in a suitable organic solvent such as THF using an amide base such as LDA, LiHMDS, NaHMDS, or KHMDS at appropriate temperatures (−78° C. to room temperature). Esterification can be achieved by standard methods including but not to limited to Fisher esterification (MeOH, $H_2SO_4$), reaction with $TMSCHN_2$ or TMSCl in MeOH. The preparation of acetylbenzoic acid ester intermediate 3 is prepared by palladium mediated coupling followed by hydrolysis. The intermediate 3 is prepared by Sonagashira coupling of the bromide 2 using an appropriately substituted acetylene, CuI, an amide base, palladium catalyst and organic solvent such as DME, THF, or DMF at temperatures between 25 to 100° C. Suitable palladium catalysts include, but are not limited to, $PdCl_2$(dppf), $Pd(Ph_3P)_4$, and $Pd_2dba_3$/dppf. Suitable amine bases include, but are not limited, to $Et_3N$, Hunig's base, and diisopropyl amine. The acetylene intermediate is hydrolyzed to the ketone derivative by standard methods including but not limited to $H_2SO_4$, TFA, trifluorosulfonamide, $FeCl_3$, or $HgSO_4/H_2SO_4$. To prepare compounds where $R^8$ is Br or I, the desired halogen can be incorporated using NBS or NIS in a suitable organic solvent or mixed solvent system such as DMF, THF-MeOH, or AcOH-THF in the presence of an appropriate acid catalyst. Quinazoline 4 can be prepared by cyclization of 3 followed by saponification under standard conditions such as LiOH or NaOH in THF-MeOH. The cyclization can be accomplished by heating fluoroacetylbenzoate derivative 3 with formamidine acetate in DMA. Carboxylic acid 4 is then converted to the amide analog 5 or the hydroxamate analog 6 by standard coupling procedures including but not limited to EDCI, HOBt, or PyBOP and the appropriate amine or hydroxylamine in suitable organic solvents like DMF, THF or dichloromethane. Protecting groups, if present, are removed after coupling.

Preparation of 4-aminoquinazoline derivatives of the Formula II is shown in FIG. 2. Nitrile 7 can be prepared by palladium mediated coupling of the bromide 2 with zinc cyanide. Cyanation is performed in a suitable organic solvent such as DMA, NMP or DMF at elevated temperatures ranging from 50 to 120° C. Suitable palladium catalysts which may be employed include but not limited to $Pd(PPh_3)_4$, $PdCl_2(dppf)$, or $Pd_2dba_3$ with ligands such as dppe, dppp, dppf or BINAP. To prepare compounds where $R^8$ is Br or I, the desired halogen can be incorporated using NBS or NIS in a suitable organic solvent or mixed solvent system such as DMF, THF-MeOH, or AcOH-THF in the presence of an appropriate acid catalyst. 4-Aminoquinazoline 8 can be prepared by cyclization followed by saponification under standard conditions such as LiOH or NaOH in THF-MeOH. The cyclization can be accomplished by heating fluoroacetylbenzoate derivative 7 with formamidine acetate in DMA. Carboxylic acid 8 is then converted to the amide analog 9 or the hydroxamate analog 10 by standard coupling procedures including but not limited to EDCI, HOBt, or PyBOP and the appropriate amine or hydroxylamine in suitable organic solvents like DMF, THF or dichloromethane. Protecting groups, if present, are removed after coupling.

Figure 3:
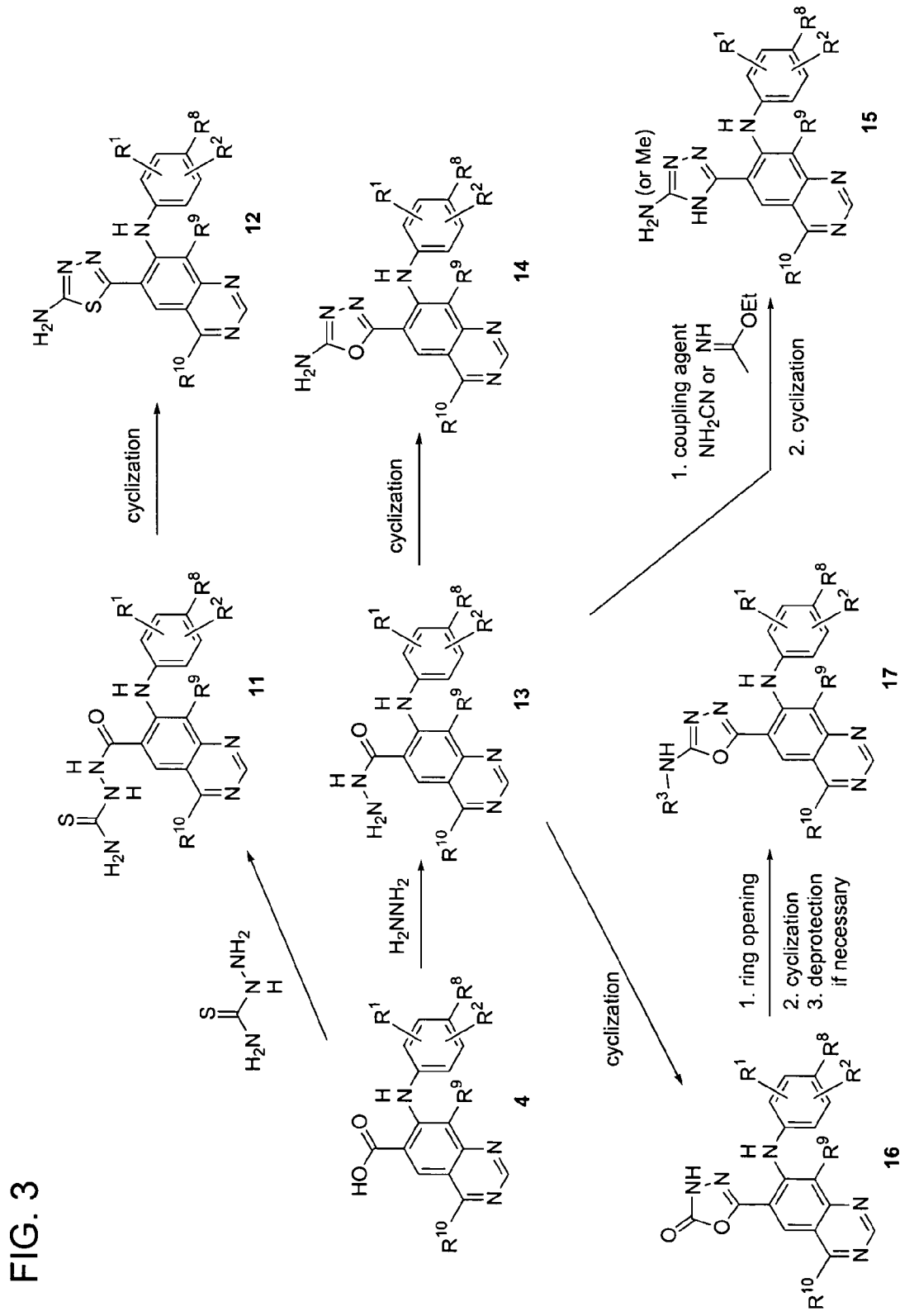
FIG. 3 shows a reaction scheme for the synthesis of compounds 11-17.

FIG. 3 illustrates the preparation of compounds of the present invention where W is a heterocyclyl. Thiazole 12 can be prepared from carboxylic acid 4 by treatment with thiosemicarbazide under standard coupling procedures (e.g., EDCI, HOBt, or PYBOP) and the appropriate hydroxylamine or amine in a suitable organic solvent such as DMF, THF or dichloromethane, followed by cyclization of the intermediate 11 employing $PPh_3$, TEA, and $CCl_4$ in dichloromethane. Alternatively, carboxylic acid 4 can be converted to the hydrazide 13 by standard coupling procedures described above. The desired heterocyclic derivatives are then prepared by cyclization with an appropriate reagent. To prepare aminooxadiazole 14, the hydrazide 13 is treated with BrCN and base such as $NaHCO_3$ in a suitable biphasic solvent system (e.g., dioxane and water) at room temperature. Triazole 15 can be prepared by reaction of the hydrazide 13 with either cyanamide or ethyl acetimidate, followed by cyclization using $PPh_3$, TEA, and $CCl_4$ in dichloromethane. For the preparation of the substituted aminooxadiazole 17 the hydrazide 13 is cyclized to the oxadiazolone 16 using CDI in DMF. The substituted aminooxadiazole 17 is then prepared by addition of an appropriate amine to the oxadiazolone 16 followed by re-cyclization of the intermediate obtained using $PPh_3$, TEA, and $CCl_4$ in dichloromethane. Additionally, the corresponding 4-aminoquinazoline analogs where W is a heterocyclyl can be prepared from carboxylic acid 8 by the above procedures.

Figure 4:
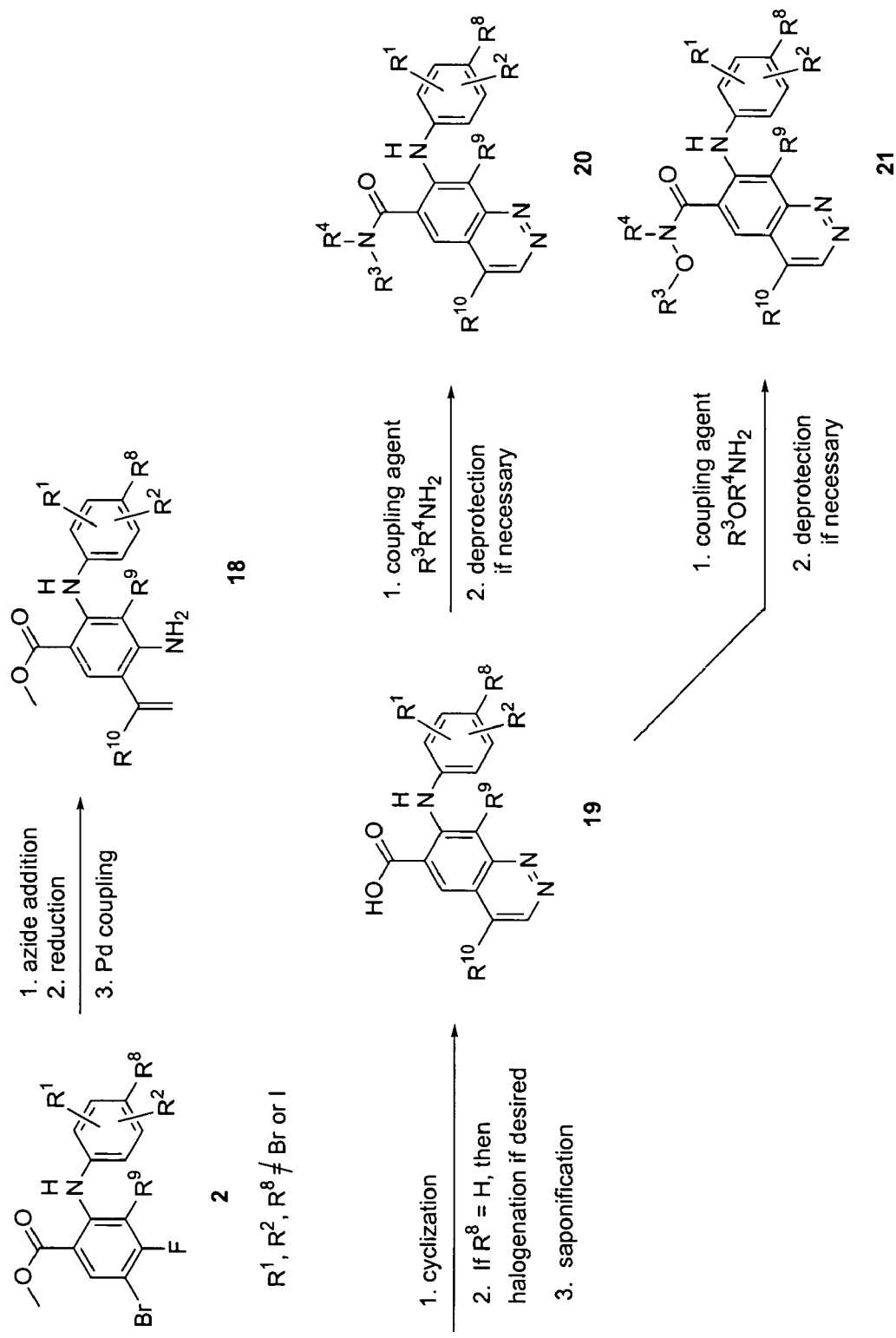
FIG. 4 shows a reaction scheme for the synthesis of compounds 19-21.

FIG. 4 illustrates another example of the synthesis of compounds of Formula I of the present invention. 5-Bromobenzoic acid methyl ester 2 is converted to 5-substituted vinyl benzoic acid ester 18 in a three-step procedure. In the first step, azide addition is accomplished using sodium azide in an appropriate solvent such as DMA or DMF at temperatures ranging from ambient temperature to 80° C. The resulting azide intermediate is reduced under standard conditions including but not limited to Zn dust/AcOH, Pt/C or $PtO_2$ in the presence of $H_2$ gas, $Ph_3P$ or $SnCl_2$/MeOH. Preferably, the azide reduction is accomplished by treatment with Zn dust in a mixture of methylene chloride and acetic acid. The vinyl group is then incorporated by a modified Suzuki coupling procedure (Molaner et al Org. Lett. 2002, 4, 107-109) using potassium isopropenyltrifluoroborate, palladium catalyst, and base in a suitable organic solvent or mixed solvent system such as toluene, DMF, dioxane, THF, MeOH, n-PrOH, or $THF\text{-}H_2O$ under reflux conditions. Suitable palladium catalysts include, but are not limited to, $PdCl_2(dppf)CH_2Cl_2$, $Pd(Ph_3P)_4$, and $Pd_2dba_3/dppf$. Suitable amine bases include, but are not limited to $Cs_2CO_3$, $K_2CO_3$, $Et_3N$, Hunig's base, and diisopropyl amine. In one embodiment, palladium mediated cross-coupling is accomplished by treatment of the bromide derivative obtained above with potassium isopropenyltrifluoroborate in the presence of $PdCl_2(dppf)CH_2Cl_2$ and $t\text{-}BuNH_2$ in $i\text{-}PrOH/H_2O$ at 70° C. Cinnoline 19 can be prepared by cyclization via diazotization of aniline 18 followed by saponification under standard conditions such as LiOH or NaOH in THF-MeOH. To prepare compounds where $R^8$ is Br or I, the desired halogen can be incorporated prior to saponification using NBS or NIS in a suitable organic solvent or mixed solvent system such as DMF, THF-MeOH, or AcOH-THF in the presence of an appropriate acid catalyst. Carboxylic acid 19 can be converted to amide analog 20 or the hydroxamate analog 21 by standard coupling procedures as outlined in FIG. 1.

FIG. 5 illustrates the preparation of 4-aminocinnoline derivatives of the Formula II. 4-Amino-6-acetyl-benzoic acid ester 22 can be prepared by azide addition followed by reduction in the same manner as described above in FIG. 4. 4-Aminocinnoline 23 can then be prepared in a four-step reaction sequence from 22. Cyclization to the corresponding 4-hydroxycinnoline is accomplished by diazotization. The amino moiety is incorporated by chlorination followed by substitution of the chloride with $NH_4OH$ or suitable amines to yield 4-amino substituted cinnoline intermediates. Chlorination of the 4-hydroxycinnoline analog can be done using $POCl_3$, thionyl chloride, oxalyl chloride or $PCl_5$. Saponification under standard conditions such as LiOH or NaOH in THF-MeOH gives 4-aminocinnoline 23. Carboxylic acid 23 can be converted to amide analog 24 or the hydroxamate analog 25 by standard coupling procedures as outlined in FIG. 1.

Figure 6:
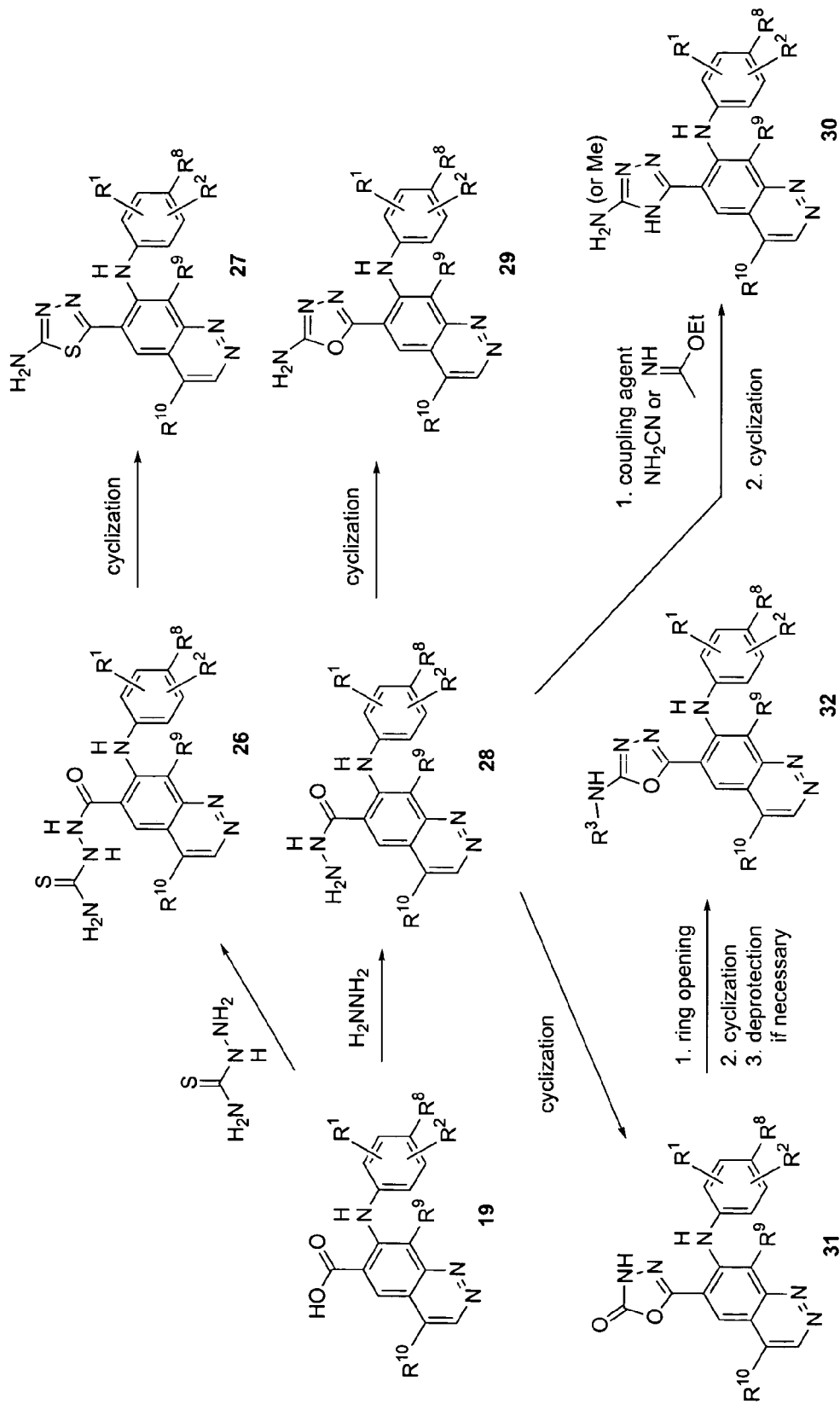
FIG. 6 shows a reaction scheme for the synthesis of compounds 26-32.

FIG. 6 illustrates the preparation of compounds of the present invention where W is heterocyclic. A variety of heterocycles such as thiazole 27, aminooxadiazole 29, triazole 30, and substituted aminooxadiazole 32 can be prepared from carboxylic acid 19 by the procedures described for FIG. 3.

Figure 7:
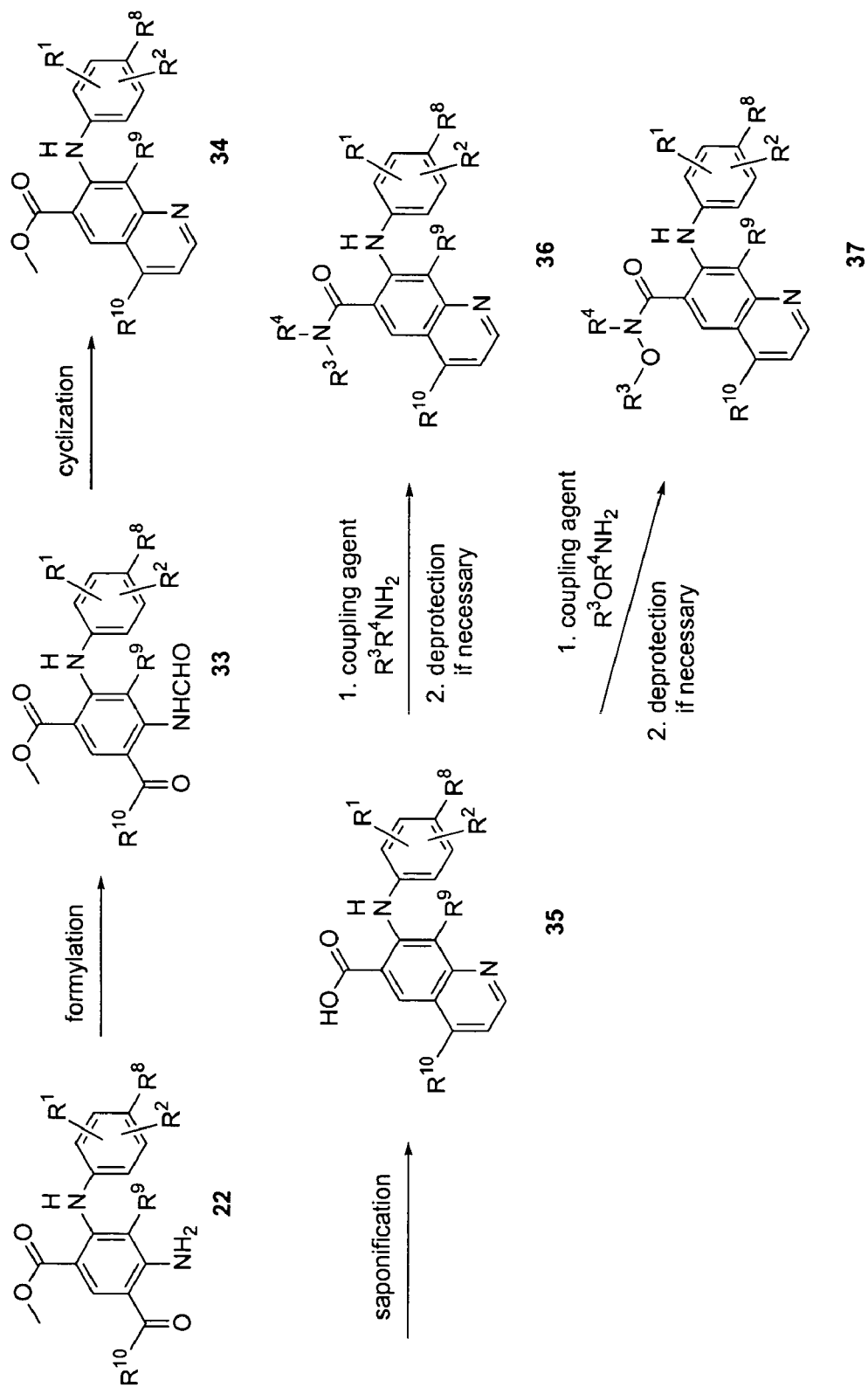
FIG. 7 shows a reaction scheme for the synthesis of compounds 35-37.

FIG. 7 illustrates the synthesis of compounds of Formula I of the present invention. 4-formylaminobenzoic acid methyl ester 33 is prepared from 4-aminobenzoic acid methyl ester 22. Formylation of 22 can be performed using formic acid, ethyl formate, or acetic formic anhydride in a suitable solvent or mixed solvent system such as THF, ether, toluene, or formic acid-$H_2O$. Cyclization to quinoline 34 is accomplished by the method of Curran et al (J. Org. Chem. 1984, 49, 2063-2065) in a two-step procedure. Methyl magnesium bromide is added to compound 33 to provide the corresponding secondary alcohol intermediate that is then cyclized to quinoline 34 with heating in the presence of polyphosphoric acid. Saponification to carboxylic acid 35 under standard conditions followed by a standard coupling procedure with the appropriate amine or hydroxylamine using methods described in FIG. 1 provides the amide analog 36 or the hydroxamate analog 37. Protecting groups, if present, are removed after coupling.

Preparation of 4-amino substituted quinoline derivatives of the Formula II is shown in FIG. 8. Cyclization and chlorination of 4-formylaminobenzoic acid methyl ester 33 to give 4-chloroquinoline 38 can be accomplished by treatment with chloroimminium salt in MeCN by the known procedure of Reid et al. (*Tetrahedron Lett.* 1990, 31, 1093-1096). Following addition of an appropriate amine, saponification by standard methods such as LiOH or NaOH in THF-MeOH provides carboxylic acid 39. Carboxylic acid 39 can then be converted to the amide analog 40 or the hydroxamate analog 41 by standard coupling procedures described in FIG. 1 with the appropriate amine or hydroxylamine. Protecting groups, if present, are removed after coupling.

Figure 9:
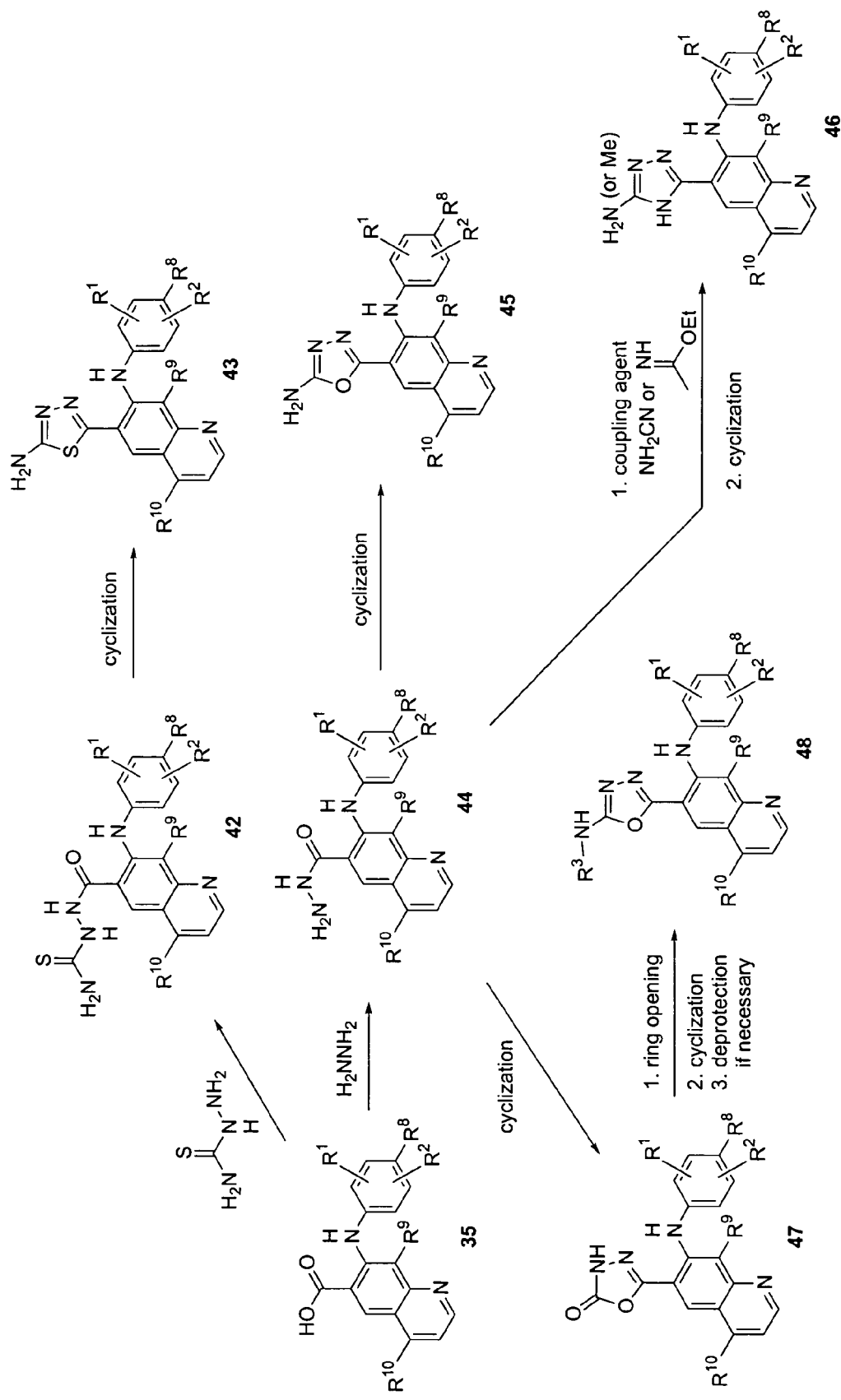
FIG. 9 shows a reaction scheme for the synthesis of compounds 42-48.

FIG. 9 illustrates the preparation of compounds of the present invention where W is a heterocyclyl. A variety of heterocycles such as thiazole 43, aminooxadiazole 45, triazole 46, and substituted aminooxadiazole 48 can be prepared from acid 35 prepared as shown in FIG. 9 by the procedures described in FIG. 3.

The invention also relates to a pharmaceutical composition for the treatment of a hyperproliferative disorder in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or the treatment of pain in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease or other inflammatory condition such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, prodrug or hydrate thereof. In one embodiment, said method relates to the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a pharmaceutical composition for treating a disease or condition related to inflammatory disease, autoimmune disease, destructive bone disorders, proliferative disorders, infectious disease, viral disease, fibrotic disease or neurodegenerative disease in a mammal which comprises a therapeutically effective amount of a compound of the present invention, or a pharmaceutically acceptable salt, prodrug or hydrate thereof, and a pharmaceutically acceptable carrier. Examples of the above diseases and/or conditions include but is not limited to rheumatoid arthritis, atherosclerosis, inflammatory bowel disease, skin diseases such as psoriasis, eczema, and scleroderma, diabetes and diabetic complications, diabetic retinopathy, retinopathy of prematurity, age-related macular degeneration, hemangioma, chronic obstructive pulmonary disease, idiopathic pulmonary fibrosis, allergic responses including asthma allergic rhinitis and atopic dermatitis, renal disease and renal failure, polycystic kidney disease, acute coronary syndrome, congestive heart failure, osteoarthritis, neurofibromatosis, organ transplant rejection, cachexia and pain.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloprotienase inhibitors are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of MEK, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I-II or a pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-II, or a pharmaceutically acceptable salt or prodrug thereof, as defined hereinbefore in association with a pharmaceutically acceptable diluent or carrier.

To prepare the pharmaceutical compositions according to this invention, a therapeutically or prophylactically effective amount of a compound of Formula I-V or a pharmaceutically acceptable salt, solvate, metabolite or prodrug thereof (alone or together with an additional therapeutic agent) is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I-V, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I-II will naturally vary according to the nature and severity of the conditions, the age and sex of the animal or patient and the route of administration, according to well known principles of medicine.

The compounds of this invention may be used alone in combination with other drugs and therapies used in the treatment of disease states which would benefit from the inhibition of MEK. Such treatment may involve, in addition to the compounds of the invention, conventional surgery or radiotherapy or chemotherapy. Such chemotherapy may include one or more of the following categories of anti-tumor agents:

(i) antiproliferative/anti-neoplastic drugs and combinations thereof, as used in medical oncology, such as alkylating agents (for example, cis-platin, carboplatin, cyclophosphamide, nitrogen mustard, melphalan, chlorambucil, busulphan and nitorsoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example epipodophyllotoxins like eptoposide and teniposide, amsacrine, topotecan and campothecin);

(ii) cytostatic agents such as antiestrogens (for example, tamoxifen, toremifene, raloxifene, droloxifene and iodoxyfene), estrogen receptor down regulators (for example, fulvestratrant) antiandrogens (for example, bicalutamide, flutamide, nilutamide, cyproxerone acetate and Casodex™ (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, asanastrozole, letrozole, vorazole and exemestane) and inhibitors of 5α-reductase such as finasteride;

(iii) agents which inhibit cancer cell invasion (for example, metalloproteinase inhibitors like marimastat and inhibitors of urokinase plasminogne activator receptor function);

(iv) inhibitors of growth factor function like growth factor antibodies, growth factor receptor antibodies (for example, the anti-erbB2 antibody trastumuzab [Herceptin™] and the anti-erbB1 antibody cetuximab [C225]), famesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), inhibitors of the platelet-derived growth factor family and inhibitors of the hepatocyte growth factor family;

(v) antiangiogenic agents such as those which inhibit the effects of vascular endothelial growth factor (for example, the anti-vascular endothelial cell growth factor antibody bevacizumab [Avastin™], compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon; and (x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies.

Such conjoint treatment may be achieved by way of the simultaneous, sequential or separate dosing of the individual components of treatment. Such combination products employ the compounds of this invention within the dose range described hereinbefore and the other pharmaceutically active agent within its approved dose range.

According to this aspect of the invention there is provided a pharmaceutical product comprising a compound of Formula I-II as defined hereinbefore and an additional anti-tumor agent as defined hereinbefore for the conjoint treatment of cancer.

Although the compounds of Formula I-II are primarily of value as therapeutic agents for use in warm-blooded animals (including man), they are also useful whenever it is required to inhibit the effects of MEK. Thus, they are useful as pharmacological standards for use in the development of new biological tests and in the search for new pharmacological agents.

The activity of the compounds of the present invention may be determined by the following procedure. N-terminal 6 His-tagged, constitutively active MEK-1 (2-393) is expressed in *E. coli* and protein is purified by conventional methods (Ahn et al., *Science* 1994, 265, 966-970). The activity of MEK1 is assessed by measuring the incorporation of γ-$^{33}$P-phosphate from γ-$^{33}$P-ATP onto N-terminal His tagged ERK2, which is expressed in *E. coli* and is purified by conventional methods, in the presence of MEK-1. The assay is carried out in 96-well polypropylene plate. The incubation mixture (100 μL) comprises of 25 mM Hepes, pH 7.4, 10 mM MgCl$_2$, 5 mM β-glycerolphosphate, 100 μM Na-orthovanadate, 5 mM DTT, 5 nM MEK1, and 1 μM ERK2. Inhibitors are suspended in DMSO, and all reactions, including controls are performed at a final concentration of 1% DMSO. Reactions are initiated by the addition of 10 μM ATP (with 0.5 μCi γ-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvester. Plates are allowed to air-dry prior to adding 30 μL/well of Packard Microscint 20, and plates are counted using a Packard TopCount. In this assay, compounds of the invention exhibited an IC$_{50}$ of less than 50 micromolar.

Representative compounds of the present invention, which are encompassed by the present invention include, but are not limited to the compounds of the examples and their pharmaceutically acceptable acid or base addition salts or prodrugs thereof. The examples presented below are intended to illustrate particular embodiments of the invention, and are not intended to limit the scope of the specification or the claims in any way.

The disclosures in this application of all articles and references, including patents, are incorporated herein by reference.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a VARIAN instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

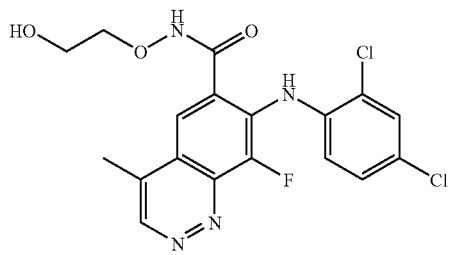

7-(2,4-Dichlorophenylamino)-8-fluoro-4-methyl-cinnoline-6-carboxylic acid (2-hydroxyethoxy)-amide Step A: Preparation of 5-bromo-2,3,4-trifluorobenzoic acid. 5-Bromo-2,3,4-trifluorobenzoic acid was prepared from 1-bromo-2,3,4-trifluorobenzene (21.3 g, 99.9 mmol) according to the procedure of Barrett et al. (WO 99/01426) to give 20.0 g (78%) of the desired product.

Step B: Preparation of 5-bromo-2-(2-chlorophenylamino)-3,4-difluorobenzoic acid. To a solution of i-Pr$_2$NH (25.0 mL, 178 mmol) in THF (200 mL) at 0° C. was added n-BuLi (71.0 mL, 178 mmol, 2.5 M solution in hexanes). After stirring for 15 minutes, this solution was cooled to −78° C. 2-Chloroaniline (12.7 mL, 118 mmol) was added. After vigorous stirring for 10 minutes, a solution of 5-bromo-2,3,4-trifluorobenzoic acid (14.95 g, 58.63 mmol) in THF (30 mL) was added. The dry-ice bath was removed, and the reaction mixture was stirred for 2 hours at room temperature. The mixture was concentrated, treated with 10% aqueous HCl (120 mL), extracted with EtOAc, dried over $MgSO_4$, filtered, and concentrated to give the crude solid which was triturated with boiling $CH_2Cl_2$ (125 mL). The yellow solids were filtered, and dried in vacuo to give the desired product (17.4 g, 82%).

Step C: Preparation of 5-bromo-2-(2-chlorophenylamino)-3,4-difluorobenzoic acid methyl ester. To a solution of 5-bromo-2-(2-chlorophenylamino)-3,4-difluorobenzoic acid (17.4 g, 48.1 mmol) in THF-MeOH (100 mL-30 mL) was added $TMSCHN_2$ (31.0 mL, 62.0 mmol, 2M solution in hexanes) at room temperature. The resulting mixture was stirred for 2 hours, quenched with AcOH, and diluted with EtOAc. The organic layer was washed with water, saturated $NaHCO_3$ (2×), and brine. The organic layer was dried over $MgSO_4$, filtered, and concentrated to give the crude product (18.0 g, 99%) that was used directly without further purification.

Step D: Preparation of 5-Bromo-2-(2,4-dichlorophenylamino)-3,4-difluorobenzoic acid methyl ester. A mixture of 5-bromo-2-(2-chlorophenylamino)-3,4-difluorobenzoic acid methyl ester (2.07 g, 5.50 mmol), NCS (789 mg, 5.91 mmol), and catalytic amount of conc. HCl in DMF (41 mL) was stirred for 1 hour at room temperature. The reaction mixture was diluted with EtOAc, and washed with water (5×). The organic layer was dried over $MgSO_4$, filtered, and concentrated to give the crude material which was purified by silica gel flash column chromatography (3 to 5% EtOAc in hexanes) to afford the desired product (2.02 g, 89%).

Step E: Preparation of 4-azido-5-bromo-2-(2 4-dichlorophenylamino)-3-fluorobenzoic acid methyl ester. A mixture of 5-bromo-2-(2,4-dichlorophenylamino)-3,4-difluorobenzoic acid methyl ester (2.02 g, 4.91 mmol) and $NaN_3$ (379 mg, 5.83 mmol) in DMA (40 mL) was heated at 50° C. for 3 hours. The reaction mixture was diluted with EtOAc, and washed with water (5×). The organic layer was dried over $MgSO_4$, filtered, and concentrated in vacuo to give the desired product (2.05 g, 96%) that was used directly without further purification.

Step F: Preparation of 4-amino-5-bromo-2-(2,4-dichlorophenylamino)-3-flourobenzoic acid methyl ester. To a mixture of 4-azido-5-bromo-2-(2,4-dichlorophenylamino)-3-fluorobenzoic acid methyl ester (2.05 g, 4.72 mmol) in $AcOH-CH_2Cl_2$ (10-30 mL) was added Zn dust (1.59 g, 24.3 mmol) at 0° C. The reaction mixture was warmed to room temperature. The resulting mixture was stirred for 1 hour. The reaction mixture was diluted with $CH_2Cl_2$, and washed with water, saturated aqueous $NaHCO_3$ (2×), water, and brine. The organic layer was dried over $MgSO_4$, filtered, and concentrated in vacuo to give the crude material which was purified by silica gel flash column chromatography(3 to 5% EtOAc in hexanes) to afford the desired product (1.24 g, 64%).

Step G: Preparation of 4-amino-2-(2,4-dichlorophenylamino)-3-fluoro-5-isopropenyl-benzoic acid methyl ester. A mixture of 4-amino-5-bromo-2-(2,4-dichlorophenylamino)-3-fluorobenzoic acid methyl ester (502 mg, 1.23 mmol), potassium isopropenyl trifluoroborate (218 mg, 1.47 mmol, Org. Lett. 2002, 4, 107), $PdCl_2(dppf)CH_2Cl_2$ (101 mg, 0.122 mmol), and $t-BuNH_2$ (0.39 mL, 3.67 mmol) in $i-PrOH-H_2O$ (2:1, 12 mL) was refluxed for 16 hours. The reaction mixture was diluted with EtOAc, washed with water, dried over $MgSO_4$, filtered, and concentrated in vacuo to give the crude material which was purified by silica gel flash column chromatography (20% $CH_2Cl_2$ in hexanes) to give the desired product (225 mg, 49%).

Step H: Preparation of 7-(2,4-dichlorophenylamino)-8-fluoro-4-methyl-cinnoline-6-carboxylic acid methyl ester. To a solution of 4-amino-2-(2,4-dichlorophenylamino)-3-fluoro-5-isopropenyl-benzoic acid methyl ester (89.9 mg, 0.243 mmol) in THF (2 mL) and conc. $H_2SO_4$ (0.050 mL, 0.94 mmol) was added a solution of $NaNO_2$ (24.0 mg, 0.348 mmol) in water (0.5 mL) at 0° C. The reaction temperature was kept below 5° C. during the addition. The reaction mixture was warmed to room temperature, and 2 mL of water was added. After stirring in the dark for 4 days, the reaction mixture was diluted with EtOAc, and washed with water. The organic layer was separated, dried over $MgSO_4$, filtered, and concentrated in vacuo to give the crude material which was purified by silica gel flash column chromatography (100% $CH_2Cl_2$ to 1% MeOH in $CH_2Cl_2$) to afford the desired product (54 mg, 58%).

Step I: Preparation of 7-(2,4-dichlorophenylamino)-8-fluoro-4-methyl-cinnoline-6-carboxylic acid. To a solution of 7-(2,4-dichlorophenylamino)-8-fluoro-4-methyl-cinnoline-6-carboxylic acid methyl ester (54 mg, 0.14 mmol) in THF-water (3 mL/1 mL) was added 1 N aqueous LiOH (0.30 mL, 0.30 mmol) at room temperature. After 30 minutes, the reaction mixture was adjusted to pH 6-7 with 1 N aqueous HCl, diluted with water, and extracted with EtOAc-THF. The organic layer was washed with water, dried over $MgSO_4$, filtered, and concentrated in vacuo to give 31 mg (60%) of the crude product (31 mg, 60%), which was used directly without further purification.

Step J: Preparation of 7-(2,4-dichlorophenylamino)-8-fluoro-4-methyl-cinnoline-6-carboxylic acid (2-hydroxyethoxy)-amide. A mixture of 7-(2,4-dichlorophenylamino)-8-fluoro-4-methyl-cinnoline-6-carboxylic acid (31 mg, 0.086 mmol), EDCI (28 mg, 0.14 mmol), and $HOBt-H_2O$ (21 mg, 0.14 mmol) in DMF (1 mL) was stirred for 45 minutes at room temperature. O-(2-Vinyloxy-ethyl)-hydroxylamine (18 mg, 0.18 mmol) and TEA (0.030 mL, 0.21 mmol) were added. The resulting mixture was stirred for 16 hours at room temperature. The reaction mixture was diluted with EtOAc, and washed with saturated aqueous $NH_4Cl$, brine, saturated aqueous $NaHCO_3$, and brine. The organic layer was dried over $MgSO_4$, filtered, and concentrated in vacuo to give the crude material which was purified by Biotage (1.5 to 3% MeOH in $CH_2Cl_2$) to afford 9 mg (39%) of 7-(2,4-dichlorophenylamino)-8-fluoro-4-methyl-cinnoline-6-carboxylic acid (2-vinyloxy-ethoxy)-amide. A mixture of the vinyl ether (9 mg, 0.020 mmol) and 1 N aqueous HCl (0.040 mL, 0.040 mmol) in EtOH (3 mL) was stirred for 1 hour at room temperature. The pH of the reaction mixture was adjusted to 6 to 7 with 2 N aqueous NaOH. The reaction mixture was diluted with EtOAc, and washed with water. The organic layer was dried over $MgSO_4$, filtered, and concentrated in vacuo to give 7-(2,4-dichlorophenylamino)-8-fluoro-4-methyl-cinnoline-6-carboxylic acid (2-hydroxyethoxy)-amide (6 mg, 71%). MS APCI (+) m/z 425, 427 (M+, Cl pattern) detected; $^1H$ NMR (400 MHz, $CD_3OD$) δ 9.26 (s, 1H), 8.30 (s 1H), 7.48 (d, 1H), 7.22 (dd, 1H), 6.90 (dd, 1H), 4.08 (t, 2H), 3.99 (t, 2H), 2.80 (s, 3H).

Example 2

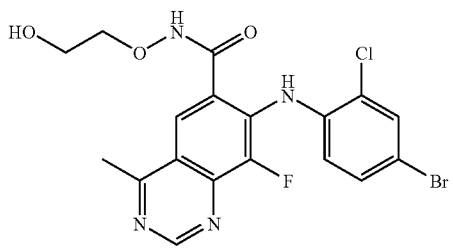

7-(4-Bromo-2-chlorophenylamino)-8-fluoro-4-methylquinazoline-6-carboxylic acid (2-hydroxyethoxy)-amide Step A: Preparation of 2-(2-chlorophenylamino)-3,4-difluoro-5-trimethylsilanylethynyl-benzoic acid methyl ester. A mixture of 5-bromo-2-(2-chlorophenylamino)-3,4-difluorobenzoic acid methyl ester (8.02 g, 21.3 mmol, prepared as described in Example 1), TMS-acetylene (3.80 mL, 26.4 mmol), Pd(PPh$_3$)$_2$Cl$_2$ (1.52 g, 2.12 mmol), CuI (405 mg, 2.12 mmol), and i-Pr$_2$NH (6.00 mL, 42.6 mmol) in THF (120 mL) was stirred for 3 days at room temperature. The reaction mixture was concentrated in vacuo, diluted with EtOAc, and washed with saturated aqueous NH$_4$Cl and brine. The organic layer was dried over MgSO4, and filtered. The organic layer was concentrated to give the crude material which was purified by silica gel flash column chromatography (100% Hexane to 1% to 2% EtOAc in Hexane) to afford the desired product (7.11 g, 85%).

Step B: Preparation of 5-acetyl-2-(2-chlorophenylamino)-3,4-difluorobenzoic acid methyl ester. A mixture of 2-(2-chlorophenylamino)-3,4-difluoro-5-trimethylsilanylethynylbenzoic acid methyl ester (7.11 g, 18.1 mmol), HgSO$_4$ (5.43 g, 18.1 mmol), and conc. H$_2$SO$_4$ (1.92 mL, 36.1 mmol) in acetone-water (150 mL/25 mL) was refluxed for 3 hours. The reaction mixture was concentrated in vacuo, diluted with EtOAc-THF, and washed with water and brine. The organic layer was dried over MgSO$_4$, filtered, and concentrated in vacuo to give the crude material which was triturated with MeOH to afford the desired product (4.46 g, 73%).

Step C: Preparation of 5-acetyl-2-(4-bromo-2-chlorophenylamino)-3,4-difluorobenzoic acid methyl ester. A mixture of 5-acetyl-2-(2-chlorophenylamino)-3,4-difluorobenzoic acid methyl ester (251 mg, 0.739 mmol), NBS (139 mg, 0.781 mmol), and catalytic amount of HBr (48%) in DMF (3 mL) was stirred for 19 hours at room temperature. The reaction mixture was diluted with EtOAc, and washed with water (5×). The organic layer was dried over MgSO$_4$, filtered, and concentrated to give the desired product (269 mg, 87%) that was used directly without further purification.

Step D: Preparation of 7-(4-bromo-2-chlorophenylamino)-8-fluoro-4-methylquinazoline-6-carboxylic acid methyl ester. A mixture of 5-acetyl-2-(4-bromo-2-chlorophenylamino)-3,4-difluorobenzoic acid methyl ester (288 mg, 0.688 mmol) and formamidine acetate (77 mg, 0.74 mmol) in DMA (7 mL) was heated for 4 hours at 95° C. Additional 10 mg (0.096 mmol) of formamidine acetate was added and the reaction mixture was heated for additional 4 hours at 95° C. The reaction mixture was diluted with EtOAc, and washed with water (3×). The organic layer was dried over MgSO$_4$, filtered, and concentrated in vacuo to give the crude material which was purified by silica gel flash column chromatography (100% CH$_2$Cl$_2$ to 1% MeOH in CH$_2$Cl$_2$) to afford the desired product (140 mg, 48%).

Step E: Preparation of 7-(4-bromo-2-chlorophenylamino)-8-fluoro-4-methylquinazoline-6-carboxylic acid. To a solution of 7-(4-bromo-2-chlorophenylamino)-8-fluoro-4-methylquinazoline-6-carboxylic acid methyl ester (137 mg, 0.323 mmol) in THF-water (3 mL/1 mL) was added 1 M aqueous LiOH (0.67 mL, 0.67 mmol) at room temperature. The resulting mixture was stirred for 2 hours at room temperature. The reaction mixture was acidified to pH 6 with 1 N aqueous HCl, diluted with water, and extracted with EtOAc. The organic layer was washed with water, dried over MgSO$_4$, filtered, and concentrated in vacuo to give the desired product (96 mg, 73%).

Step F: Preparation of 7-(4-bromo-2-chlorophenylamino)-8-fluoro-4-methylquinazoline-6-carboxylic acid (2-hydroxyethoxy)-amide. To a solution of 7-(4-bromo-2-chlorophenylamino)-8-fluoro-4-methylquinazoline-6-carboxylic acid (47 mg, 0.11 mmol) in DMF (2 mL) was added HOBt (26.0 mg, 0.170 mmol), Et$_3$N (0.060 mL, 0.044 mmol), O-(2-vinyloxy-ethyl)-hydroxylamine (15 mg, 0.15 mmol), and EDCI (30 mg, 0.16 mmol) at room temperature. The resulting solution was stirred for 7 days at room temperature. The reaction mixture was diluted with EtOAc, and washed with saturated aqueous NH$_4$Cl, brine, saturated aqueous NaHCO$_3$, and brine. The organic layer was dried over MgSO$_4$, filtered, concentrated in vacuo to give the crude material which was purified by silica gel flash column chromatography (1.5 to 2% MeOH in CH$_2$Cl$_2$) to afford 24 mg (42%) of 7-(4-bromo-2-chlorophenylamino)-8-fluoro-4-methylquinazoline-6-carboxylic acid (2-vinyloxy-ethoxy)-amide. To a solution of the vinyl ether (24.0 mg, 0.048 mmol) in EtOH (2 mL) was added 1 N aqueous HCl (0.21 mL) at room temperature. After stirring for 3 hours at room temperature, pH of the reaction mixture was adjusted to 6 to 7 with 1 N aqueous NaOH, and extracted with EtOAc. The organic layer was washed with water, dried over MgSO$_4$, filtered, and concentrated in vacuo to give the crude material which was purified by silica gel flash column chromatography (5 to 10 to 20% MeOH in CH$_2$Cl$_2$ with 1% Et$_3$N) to afford 7-(4-bromo-2-chlorophenylamino)-8-fluoro-4-methylquinazoline-6-carboxylic acid (2-hydroxyethoxy)-amide (5 mg, 22%). MS APCI (−) m/z 467, 469 (M-, Br, Cl pattern) detected; $^1$H NMR (400 MHz, CD$_3$OD) δ 9.06 (s, 1H), 8.38 (s, 1H), 7.60 (d, 1H), 7.35 (dd, 1H), 6.86 (dd, 1H), 4.10 (t, 2H), 3.81 (t, 2H), 2.99 (s, 3H).

Example 3

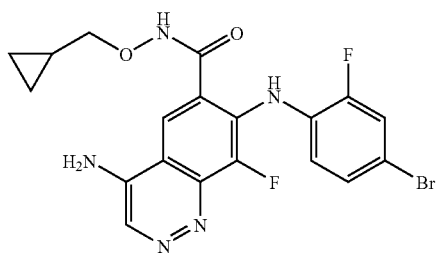

4-Amino-7-(4-bromo-2-fluorophenylamino)-8-fluoro-cinnoline-6-carboxylic acid cyclopropyl-methoxy-amide Step A: Preparation of 5-bromo-3,4-difluoro-2-(2-fluorophenylamino)-benzoic acid: The title compound is prepared from 5-bromo-2,3,4-trifluorobenzoic acid prepared in step A for Example 1 by the procedure described in step B for Example 1 using 4-fluoroaniline in place of 4-chloroaniline.

Step B: Preparation of 5-bromo-3,4-difluoro-2-(2-fluorophenylamino)-benzoic acid methyl ester: The title compound is prepared from 5-bromo-3,4-difluoro-2-(2-fluorophenylamino)-benzoic acid by the method described in step C for Example 1.

Step C: Preparation of 3,4-difluoro-2-(2-fluorophenylamino)-5-trimethylsilanylethynyl-benzoic acid methyl ester: The title compound is prepared from 5-bromo-3,4-difluoro-2-(2-fluorophenylamino)-benzoic acid methyl ester in the same manner as previously described in step A for Example 2.

Step D: Preparation of 5-acetyl-3,4-difluoro-2-(2-fluorophenylamino)-benzoic acid methyl ester: The title compound is prepared from 3,4-difluoro-2-(2-fluorophenylamino)-5-trimethylsilanylethynyl-benzoic acid methyl ester by the method previously described in step B for Example 2.

Step E: Preparation of 5-acetyl-2-(4-bromo-2-fluorophenylamino)-3,4-difluorobenzoic acid methyl ester: The title compound is prepared from 5-acetyl-3,4-difluoro-2-(2-fluorophenylamino)-benzoic acid methyl ester by the procedure previously described in step C for Example 2.

Step F: Preparation of 5-acetyl-4-azido-2-(4-bromo-2-fluorophenylamino)-3-fluorobenzoic acid methyl ester: The title compound is prepared from 5-acetyl-2-(4-bromo-2-fluorophenylamino)-3,4-difluorobenzoic acid methyl ester in an analogous manner described in step E for Example 1.

Step G: Preparation of 5-acetyl-4-amino-2-(4-bromo-2-fluorophenylamino)-3-fluorobenzoic acid methyl ester: The title compound is prepared from 5-acetyl-4-azido-2-(4-bromo-2-fluorophenylamino)-3-fluorobenzoic acid methyl ester in the method previously described in step F for Example 1.

Step H: Preparation of 7-(4-bromo-2-fluorophenylamino)-8-fluoro-4-hydroxy-cinnoline-6-carboxylic acid methyl ester: To a solution of 5-acetyl-4-amino-2-(4-bromo-2-fluorophenylamino)-3-fluorobenzoic acid methyl ester (1.00 equiv.) in THF and conc $H_2SO_4$ (4.00 equiv.) is added a solution of $NaNO_2$ (1.50 equiv.) in water at 0° C. The reaction mixture is warmed to 60° C. and stirred for 3 hours. The reaction mixture is cooled to room temperature and diluted with EtOAc. The organic layer is washed with water, dried over $MgSO_4$, filtered, and concentrated in vacuo to give the crude material that is purified by flash column chromatography to afford the desired product as necessary.

Step I: Preparation of 7-(4-bromo-2-fluorophenylamino)-4-chloro-8-fluoro-cinnoline-6-carboxylic acid methyl ester: A mixture of 7-(4-bromo-2-fluorophenylamino)-8-fluoro-4-hydroxy-cinnoline-6-carboxylic acid methyl ester (1.00 equiv.) and $POCl_3$ (excess) is stirred for 1.5 hours at 80° C. After evaporation of $POCl_3$ under reduced pressure, the crude material is poured into ice and neutralized to pH 7 to 8 with saturated aqueous $NaHCO_3$. The aqueous layer is extracted with EtOAc. The organic layers is dried over $MgSO_4$, filtered, and concentrated under reduced pressure to give the crude product that is purified by trituration or flash column chromatography to afford the desired product as necessary.

Step J: Preparation of 4-amino-7-(4-bromo-2-fluorophenylamino)-8-fluoro-cinnoline-6-carboxylic acid methyl ester: A solution of 7-(4-bromo-2-fluorophenylamino)-4-chloro-8-fluoro-cinnoline-6-carboxylic acid methyl ester (1.00 equiv.) in saturated $NH_3$ in MeOH is refluxed for 16 hours. Additional saturated $NH_3$ in MeOH is added as the reaction progresses if necessary. The reaction mixture is cooled to room temperature and diluted with EtOAc. The organic layer is washed with brine, dried over $MgSO_4$, filtered, and concentrated under reduced pressure to give the crude product that is purified by trituration or flash column chromatography to afford the desired product as necessary.

Step K: Preparation of 4-amino-7-(4-bromo-2-fluorophenylamino)-8-fluoro-cinnoline-6-carboxylic acid: The title compound is prepared from 4-amino-7-(4-bromo-2-fluorophenylamino)-8-fluoro-cinnoline-6-carboxylic acid methyl ester by the procedure previously described in step I for Example 1.

Step L: Preparation of 4-amino-7-(4-bromo-2-fluorophenylamino)-8-fluoro-cinnoline-6-carboxylic acid cyclopropylmethoxy-amide: The title compound is prepared from 4-amino-7-(4-bromo-2-fluorophenylamino)-8-fluoro-cinnoline-6-carboxylic acid by the procedure previously described in step J for Example 1 using 0-cyclopropylmethyl-hydroxylamine in place of O-(2-vinyloxyethyl)-hydroxylamine.

Example 4

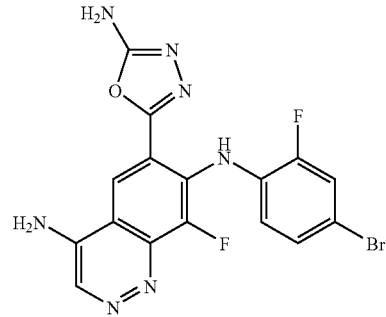

6-(5-Amino-[1,3,4]oxadiazol-2-yl)-N7-(4-bromo-2-fluorophenyl)-8-fluorocinnoline-4,7-diamine Step A: Preparation of 4-amino-7-(4-bromo-2-fluorophenylamino)-8-fluorocinnoline-6-carboxylic acid hydrazide: To a solution of 4-amino-7-(4-bromo-2-fluorophenylamino)-8-fluoro-cinnoline-6-carboxylic acid (1.00 equiv.) and HOBt (3.00 equiv.) in DMF is added EDCI (3.00 equiv.) at room temperature. After stirring for 1 hour, hydrazine (3.00 equiv.) and TEA (3.00 equiv.) are added. The reaction mixture is stirred for 1 hour and diluted with EtOAc. The resulting mixture is washed with saturated aqueous $NH_4Cl$, brine, saturated aqueous $NaHCO_3$, and brine. The organic layer is dried over $MgSO_4$, filtered, and concentrated under reduced pressure to give the crude material that is used directly without further purification.

Step B: Preparation of 6-(5-amino-[1,3,4]oxadiazol-2-yl)-N7-(4-bromo-2-fluoro-phenyl)-8-fluoro-cinnoline-4,7-diamine: To a suspension of 4-amino-7-(4-bromo-2-fluorophenylamino)-8-fluorocinnoline-6-carboxylic acid hydrazide (1.00 equiv.) in 1,4-dioxane at room temperature is added BrCN (2.00 equiv.) followed by a solution of $NaHCO_3$ (1.00 equiv.) in $H_2O$. After stirring for 3 hours at room temperature, the reaction mixture is diluted with water and extracted with EtOAc. The organic layer is washed with brine, dried over MgSO₄, filtered, and concentrated under reduced pressure to give the crude material that is purified by trituration or flash column chromatography to afford 6-(5-amino-[1,3,4]oxadiazol-2-yl)-N7-(4-bromo-2-fluoro-phenyl)-8-fluorocinnoline-4,7-diamine.

Example 5

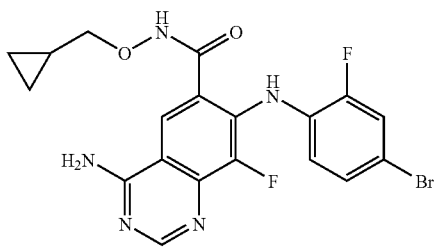

4-Amino-7-(4-bromo-2-fluorophenylamino)-8-fluoroquinazoline-6-carboxylic acid cyclopropyl-methoxy-amide Step A: Preparation of 5-cyano-3,4-difluoro-2-(2-fluorophenylamino)-benzoic acid methyl ester: A mixture of 5-bromo-3,4-difluoro-2-(2-fluorophenylamino)-benzoic acid methyl ester (1.00 equiv.), dppf (0.02 equiv.), Pd₂dba₃ (0.01 equiv.), and Zn(CN)₂ (0.60 equiv.) in NMP is stirred at 120° C. in a sealed tube. After stirring for 20 hours, the reaction mixture is cooled to room temperature and quenched with a 4:1:4 (volume) mixture solution of saturated aqueous NH₄Cl-conc NH₄O-water. The mixture is extracted with EtOAc. The organic layer is washed with saturated aqueous NH₄Cl/concentrated NH₄OH/water, and brine. The organic layer is dried over MgSO₄, filtered, and concentrated under reduced pressure to give the crude material that is purified by flash column chromatography to afford the desired product.

Step B: Preparation of 2-(4-bromo-2-fluorophenylamino)-5-cyano-3,4-difluorobenzoic acid methyl ester: The title compound is prepared from 5-cyano-3,4-difluoro-2-(2-fluorophenylamino)-benzoic acid methyl ester by the procedure previously described in step C for Example 2.

Step C: Preparation of 4-amino-7-(4-bromo-2-fluorophenylamino)-8-fluoroquinazoline-6-carboxylic acid methyl ester: The title compound is prepared from 2-(4-bromo-2-fluorophenylamino)-5-cyano-3,4-difluorobenzoic acid methyl ester in an analogous manner by the method previously described in step D for Example 2.

Step D: Preparation of 4-amino-7-(4-bromo-2-fluorophenylamino)-8-fluoroquinazoline-6-carboxylic acid: The title compound is prepared by the procedure previously described in step I for Example 1.

Step E: Preparation of 4-amino-7-(4-bromo-2-fluorophenylamino)-8-fluoroquinazoline-6-carboxylic acid cyclopropylmethoxy-amide: The title compound is prepared in the same manner described in step J for Example 1 using O-cyclopropylmethyl-hydroxylamine in place of O-(2-vinyloxy-ethyl)-hydroxylamine.

Example 6

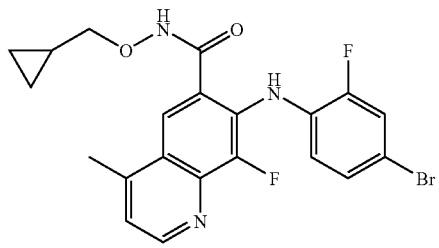

7-(4-Bromo-2-fluorophenylamino)-8-fluoro-4-methyl-quinoline-6-carboxylic acid cyclopropyl-methoxy-amide Step A: Preparation of 5-acetyl-2-(4-bromo-2-fluorophenylamino)-3-fluoro-4-formylamino-benzoic acid methyl ester: To acetic anhydride (1.30 equiv.) is added formic acid (1.60 equiv.) at room temperature. The resulting mixture is stirred at 65 OC under N₂ atmosphere for 2 hours, cooled to room temperature, and diluted with THF. To a solution of 5-acetyl-4-amino-2-(4-bromo-2-fluorophenylamino)-3-fluorobenzoic acid methyl ester (1.00 equiv.) in THF at 0° C. is added the above solution of acetic formic anhydride in THF. After stirring 30 minutes at 0° C., the reaction is quenched with MeOH. The reaction mixture is concentrated under reduced pressure to give the crude material that is purified by trituration or flash column chromatography to yield the desired product as necessary.

Step B: Preparation of 2-(4-bromo-2-fluorophenylamino)-3-fluoro-4-formylamino-5-(1-hydroxy-1-methyl-ethyl)-benzoic acid methyl ester: To a solution of MeMgBr (3.20 equiv., 3.0 M solution in diethyl ether) in ether is added a solution of 5-acetyl-2-(4-bromo-2-fluorophenylamino)-3-fluoro-4-formylamino-benzoic acid methyl ester (1.00 equiv.) in THF at 0° C. The reaction mixture is warmed to room temperature and stirred for 16 hours. The reaction is quenched with saturated aqueous NH₄Cl and diluted with EtOAc. The organic layer is washed with brine, dried over MgSO₄, filtered, and concentrated under reduced pressure to give the crude material that is used directly without further purification.

Step C: Preparation of 7-(4-bromo-2-fluorophenylamino)-8-fluoro-4-methyl-quinoline-6-carboxylic acid methyl ester: A mixture of 2-(4-bromo-2-fluorophenylamino)-3-fluoro-4-formylamino-5-(1-hydroxy-1-methyl-ethyl)-benzoic acid methyl ester (1.00 equiv.) and polyphosphoric acid is stirred at 160° C. for 20 hours. The reaction mixture is cooled to room temperature and diluted with EtOAc. The organic layer is washed with water and brine, dried over MgSO₄, filtered, and concentrated under reduced pressure to give the crude material that is purified by trituration or flash column chromatography to yield the desired product as necessary.

Step D: Preparation of 7-(4-bromo-2-fluorophenylamino)-8-fluoro-4-methyl-quinoline-6-carboxylic acid: The title compound is prepared from 7-(4-bromo-2-fluorophenylamino)-8-fluoro-4-methylquinoline-6-carboxylic acid methyl ester by the procedure previously described in step I for Example 1.

Step E: Preparation of 7-(4-bromo-2-fluorophenylamino)-8-fluoro-4-methyl-quinoline-6-carboxylic acid cyclopropylmethoxyamide: The title compound is prepared from 7-(4-bromo-2-fluorophenylamino)-8-fluoro-4-methyl-quinoline-6-carboxylic acid in the same manner described in step J for Example 1 using O-cyclopropylmethyl-hydroxylamine in place of O-(2-vinyloxy-ethyl)-hydroxylamine.

Example 7

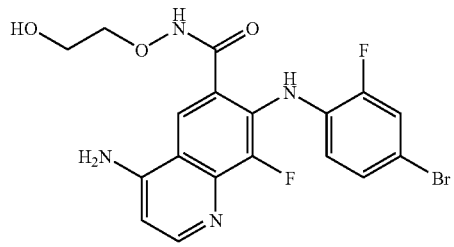

4-Amino-7-(4-bromo-2-fluorophenylamino)-8-fluoroquinoline-6-carboxylic acid (2-hydroxyethoxy)-amide Step A: Preparation of 7-(4-bromo-2-fluorophenylamino)-4-chloro-8-fluoroquinoline-6-carboxylic acid methyl ester, To a solution of 5-acetyl-2-(4-bromo-2-fluorophenylamino)-3-fluoro-4-formylamino-benzoic acid methyl ester (1.00 equiv.) in MeCN is added a solution of (chloromethylene)dimethyliminium chloride (2.50 equiv.) in MeCN at 0° C. The resulting mixture is warmed to room temperature and stirred for 16 hours. The reaction mixture is diluted with EtOAc. The organic layer is washed with water and brine, dried over MgSO₄, filtered, and concentrated under reduced pressure to give the crude material that is purified by trituration or flash column chromatography to yield the desired product as necessary.

Step B: Preparation of 4-amino-7-(4-bromo-2-fluorophenylamino)-8-fluoroquinoline-6-carboxylic acid methyl ester: The title compound is prepared from 7-(4-bromo-2-fluorophenylamino)-4-chloro-8-fluoroquinoline-6-carboxylic acid methyl ester by the procedure previously described in step J for Example 3.

Step C: Preparation of 4-amino-7-(4-bromo-2-fluorophenylamino)-8-fluoroquinoline-6-carboxylic acid: The title compound is prepared from 4-amino-7-(4-bromo-2-fluorophenylamino)-8-fluoroquinoline-6-carboxylic acid methyl ester by the procedure previously described in step I for Example 1.

Step D: Preparation of 4-amino-7-(4-bromo-2-fluorophenylamino)-8-fluoroquinoline-6-carboxylic acid (2-hydroxyethoxy)-amide: The title compound is prepared from 4-amino-7-(4-bromo-2-fluorophenylamino)-8-fluoroquinoline-6-carboxylic acid in the same manner described in step J for Example 1.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound including resolved enantiomers, diastereomers, and pharmaceutically acceptable salts thereof, said compound having the Formula:

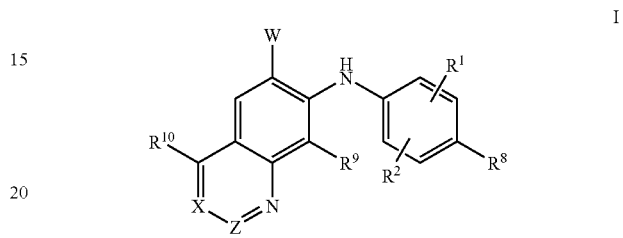

where

X is $CR^3$ and Z is N;

$R^1$, $R^2$, $R^8$, $R^9$ and $R^{10}$ are independently hydrogen, hydroxy, halogen, cyano, nitro, trifluoromethyl, difluoromethyl, fluoromethyl, trifluoromethoxy, difluoromethoxy, trifluoromethoxy, azido, —$SR^{11}$, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, and wherein any of said aryl, heteroaryl, arylalkyl, heteroarylalkyl, heterocyclyl or heterocyclylalkyl rings may be further substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl, and heterocyclylalkyl, or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl, and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic, heteroaryl or heterocyclic ring, wherein any of said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl, and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl, and heterocyclylalkyl;

$R^{11}$, $R^{12}$ and $R^{13}$ independently are hydrogen, lower alkyl, lower alkenyl, aryl or arylalkyl, and $R^{14}$ is lower alkyl, lower alkenyl, aryl or arylalkyl;

or any two of $R^{11}$, $R^{12}$, $R^{13}$ or $R^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, $-C(O)OR^3$, $-C(O)NR^3R^4$, $-C(O)NR^4OR^3$, $-C(O)R^4OR^3$, $-C(O)NR^4SO_2R^3$, $-C(O)(C_3$-$C_{10}$ cycloalkyl), $-C(O)(C_1$-$C_{10}$ alkyl), $-C(O)(aryl)$, $-C(O)(heteroaryl)$, $-C(O)(heterocyclyl)$ or $CR^3OR^3$, wherein any of said heteroaryl, heterocyclyl, $-C(O)OR^3$, $-C(O)NR^3R^4$, $-C(O)NR^4OR^3$, $-C(O)R^4OR^3$, $-C(O)NR^4SO_2R^3$, $-C(O)(C_3$-$C_{10}$ cycloalkyl), $-C(O)(C_1$-$C_{10}$ alkyl), $-C(O)(aryl)$, $-C(O)(heteroaryl)$, $-C(O)(heterocyclyl)$ and $CR^3OR^3$ are optionally substituted with one or more groups independently selected from halogen, cyano, nitro, azido, $-NR^3R^4$, $-OR^3$, $C_1$-$C_{10}$ alkyl, $C_2$-$C_{10}$ alkenyl, $C_2$-$C_{10}$ alkynyl, cycloalkyl and heterocycloalkyl, wherein any of said $C_1$-$C_{10}$ alkyl, $C_2$-$C_{10}$ alkenyl, $C_2$-$C_{10}$ alkynyl, cycloalkyl and heterocycloalkyl are optionally substituted with 1 or more groups independently selected from $-NR^3R^4$ and $-OR^3$;

m is 0, 1, 2, 3, 4 or 5; and j is 0, 1 or 2.

2. The compound of claim 1, where $R^9$ is hydrogen, halogen, methyl, fluoromethyl, difluoromethyl, trifluoromethyl or ethyl.

3. The compound of claim 2, where W is selected from heteroaryl, $C(O)OR^3$, $C(O)NR^3R^4$, $C(O)NR^4OR^3$ and $C(O)NR^4S(O)_2R^3$, wherein any of said heteroaryl, $C(O)OR^3$, $C(O)NR^3R^4$, $C(O)NR^4OR^3$ or $C(O)NR^4S(O)_2R^3$ are optionally substituted with one or more groups independently selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethoxy, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl, wherein any of said $C_1$-$C_4$ alkyl, $C_2$-$C_4$ alkenyl, $C_2$-$C_4$ alkynyl, cycloalkyl or heterocycloalkyl can be further optionally substituted with one or more groups independently selected from $NR^3R^4$ and $OR^3$.

4. The compound of claim 2, where W is selected from $C(O)OR^3$, $C(O)NHR^3$, and $C(O)NHOR^3$, wherein any of said $C(O)OR^3$, $C(O)NHR^3$, and $C(O)NHOR^3$ are optionally substituted with one or more groups independently selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethoxy, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl, wherein any of said $C_1$-$C_4$ alkyl, $C_2$-$C_4$ alkenyl, $C_2$-$C_4$ alkynyl, cycloalkyl or heterocycloalkyl can be further optionally substituted with one or more groups independently selected from $NR^3R^4$ and $OR^3$; and $R^3$ is selected from hydrogen, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl, wherein any of said $C_1$-$C_4$ alkyl, $C_2$-$C_4$ alkenyl, $C_2$-$C_4$ alkynyl, cycloalkyl or heterocycloalkyl are optionally substituted with one or more groups independently selected from $NR^3R^4$ and $OR^3$.

5. The compound of claim 4, where $R^7$ is $C_1$-$C_4$ alkyl, $C_2$-$C_4$ alkenyl or $C_2$-$C_4$ alkynyl, wherein any of said $C_1$-$C_4$ alkyl, $C_2$-$C_4$ alkenyl and $C_2$-$C_4$ alkynyl may be optionally substituted with one or more groups independently selected from halogen, hydroxyl, cyano, nitro, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl or heteroaryl, wherein any of said cycloalkyl, heterocycloalkyl, aryl or heteroaryl rings may be optionally substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$.

6. The compound of claim 5, where $R^1$ and $R^2$ are independently hydrogen, halogen, methyl, fluoromethyl, difluoromethyl, trifluoromethyl or ethyl; and $R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethyl, ethoxy or $SR^{11}$.

7. The compound of claim 6, where $R^1$ is halogen or methyl, $R^2$ is hydrogen and $R^8$ is hydrogen, halogen, methyl, fluoromethyl, difluoromethyl, trifluoromethyl or $SR^{11}$.

8. The compound of claim 7, where $R^1$ is halogen, $R^8$ is halogen, $R^9$ is alkyl or halogen, and $R^2$ is in the position adjacent to Y, where $R^2$ is hydrogen.

9. The compound of claim 2, where W is selected from

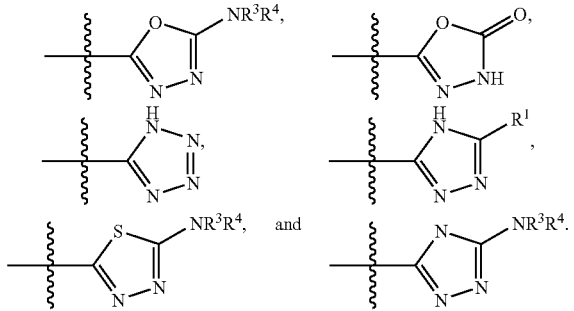

10. The compound of claim 9, where $R^7$ is $C_1$-$C_4$ alkyl, $C_2$-$C_4$ alkenyl or $C_2$-$C_4$ alkynyl, wherein any of said $C_1$-$C_4$ alkyl, $C_2$-$C_4$ alkenyl and $C_2$-$C_4$ alkynyl, may be optionally substituted with one or more groups independently selected from halogen, hydroxyl, cyano, nitro, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl and heteroaryl, wherein any of said cycloalkyl, heterocycloalkyl, aryl or heteroaryl rings may be optionally substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$.

11. The compound of claim 10, where $R^1$ and $R^2$ are independently hydrogen, halogen, methyl, fluoromethyl, difluoromethyl, trifluoromethyl or ethyl; and $R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethyl, ethoxy or $SR^{11}$.

12. The compound of claim 11, where $R^1$ is halogen or methyl, $R^2$ is hydrogen and $R^8$ is hydrogen, halogen, methyl, fluoromethyl, difluoromethyl, trifluoromethyl or $SR^{11}$.

13. The compound of claim 12, where $R^1$ is halogen, $R^8$ is halogen, $R^9$ is alkyl or halogen, and $R^2$ is in the position adjacent to Y, where $R^2$ is hydrogen.

14. The compound of claim 1, where $R^{10}$ is —$NR^7R^{15}$; and $R^7$ and $R^{15}$ are independently hydroxy, halogen, trifluoromethyl, difluoromethyl, fluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, $OR^3$, $NR^3R^4$, aryl, arylalkyl, heteroaryl, heteroarylalkyl, heterocyclyl, or heterocyclylalkyl, wherein any of said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, cycloalkyl, cycloalkylalkyl, heterocyclyl, and heterocyclylalkyl, and wherein any of said aryl, heteroaryl, arylalkyl, heteroarylalkyl, cycloalkyl, cycloalkylalkyl, heterocyclyl or heterocyclylalkyl rings may be further substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

or $R^7$ and $R^{15}$ together with the atom to which they are attached form a 4 to 10 membered aryl, carbocyclic, heteroaryl or heterocyclic ring, wherein any of said aryl, carbocyclic, heteroaryl or heterocyclic rings are optionally substituted with one or more groups independently selected from halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, cycloalkyl, cycloalkylalkyl, heterocyclyl, and heterocyclylalkyl.

15. The compound of claim 14, where $R^9$ is hydrogen, halogen, methyl, fluoromethyl, difluoromethyl, trifluoromethyl or ethyl.

16. The compound of claim 14, where W is selected from heteroaryl, $C(O)OR^3$, $C(O)NR^3R^4$, $C(O)NR^4OR^3$ and $C(O)NR^4S(O)_2R^3$, wherein any of said heteroaryl, $C(O)OR^3$, $C(O)NR^3R^4$, $C(O)NR^4OR^3$ or $C(O)NR^4S(O)_2R^3$ are optionally substituted with one or more groups independently selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethoxy, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl, wherein any of said $C_1$-$C_4$ alkyl, $C_2$-$C_4$ alkenyl, $C_2$-$C_4$ alkynyl, cycloalkyl or heterocycloalkyl can be further optionally substituted with one or more groups independently selected from $NR^3R^4$ and $OR^3$.

17. The compound of claim 14, where W is selected from $C(O)OR^3$, $C(O)NHR^3$, and $C(O)NHOR^3$, wherein any of said $C(O)OR^3$, $C(O)NHR^3$, and $C(O)NHOR^3$ are optionally substituted with one or more groups independently selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethoxy, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl, wherein any of said $C_1$-$C_4$ alkyl, $C_2$-$C_4$ alkenyl, $C_2$-$C_4$ alkynyl, cycloalkyl or heterocycloalkyl can be further optionally substituted with one or more groups independently selected from $NR^3R^4$ and $OR^3$; and $R^3$ is selected from hydrogen, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl, wherein any of said $C_1$-$C_4$ alkyl, $C_2$-$C_4$ alkenyl, $C_2$-$C_4$ alkynyl, cycloalkyl or heterocycloalkyl are optionally substituted with one or more groups independently selected from $NR^3R^4$ and $OR^3$.

18. The compound of claim 17, where $R^7$ is $C_1$-$C_4$ alkyl, $C_2$-$C_4$ alkenyl or $C_2$-$C_4$ alkynyl, wherein any of said $C_1$-$C_4$ alkyl, $C_2$-$C_4$ alkenyl and $C_2$-$C_4$ alkynyl may be optionally substituted with one or more groups independently selected from halogen, hydroxyl, cyano, nitro, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl and heteroaryl, wherein any of said cycloalkyl, heterocycloalkyl, aryl or heteroaryl rings may be optionally substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$.

19. The compound of claim 18, where $R^1$ and $R^2$ are independently hydrogen, halogen, methyl, fluoromethyl, difluoromethyl, trifluoromethyl or ethyl; and $R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethyl, ethoxy or $SR^{11}$.

20. The compound of claim 19, where $R^1$ is halogen or methyl, $R^2$ is hydrogen and $R^8$ is hydrogen, halogen, methyl, fluoromethyl, difluoromethyl, trifluoromethyl or $SR^{11}$.

21. The compound of claim 20, where $R^1$ is halogen, $R^8$ is halogen, $R^9$ is alkyl or halogen, and $R^2$ is in the position adjacent to Y, where $R^2$ is hydrogen.

22. The compound of claim 14, where W is selected from

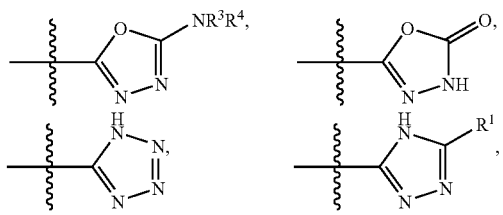

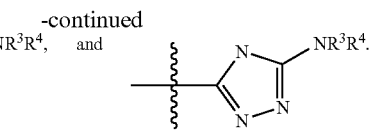

23. The compound of claim 22, where $R^7$ is $C_1$-$C_4$ alkyl, $C_2$-$C_4$ alkenyl or $C_2$-$C_4$ alkynyl, wherein any of said $C_1$-$C_4$ alkyl, $C_2$-$C_4$ alkenyl and $C_2$-$C_4$ alkynyl may be optionally substituted with one or more groups independently selected from halogen, hydroxyl, cyano, nitro, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl and heteroaryl, wherein any of said cycloalkyl, heterocycloalkyl, aryl or heteroaryl rings may be optionally substituted with one or more groups independently selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$.

24. The compound of claim 23, where $R^1$ and $R^2$ are independently hydrogen, halogen, methyl, fluoromethyl, difluoromethyl, trifluoromethyl or ethyl; and $R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethyl, ethoxy or $SR^{11}$.

25. The compound of claim 24, where $R^1$ is halogen or methyl, $R^2$ is hydrogen and $R^8$ is hydrogen, halogen, methyl, fluoromethyl, difluoromethyl, trifluoromethyl or $SR^{11}$.

26. The compound of claim 25, where $R^1$ is halogen, $R^8$ is halogen, $R^9$ is alkyl or halogen, and $R^2$ is in the position adjacent to Y, where $R^2$ is hydrogen.

27. A composition comprising a compound of claim 1 and a pharmaceutically acceptable carrier.

28. A composition comprising a compound of claim 4 and a pharmaceutically acceptable carrier.

29. A composition comprising a compound of claim 9 and a pharmaceutically acceptable carrier.

30. A composition comprising a compound of claim 14 and a pharmaceutically acceptable carrier.

31. A composition comprising a compound of claim 17 and a pharmaceutically acceptable carrier.

32. A composition comprising a compound of claim 22 and a pharmaceutically acceptable carrier.

* * * * *